US012799159B2

(12) United States Patent
Dow et al.

(10) Patent No.: US 12,799,159 B2
(45) Date of Patent: Nov. 17, 2026

(54) INSECT NEUROPEPTIDES 5

(71) Applicant: Solasta Bio Limited, Glasgow (GB)

(72) Inventors: Julian A.T. Dow, East Dunbartonshire (GB); Shireen A. Davies, East Dunbartonshire (GB); Yousef Abul-Haija, East Dunbartonshire (GB); Lewis Archibald, Glasgow (GB)

(73) Assignee: SOLASTA BIO LIMITED, Glasgow (GB)

( * ) Notice: Subject to any disclaimer, the term of this patent is extended or adjusted under 35 U.S.C. 154(b) by 0 days.

(21) Appl. No.: 18/491,958

(22) Filed: Oct. 23, 2023

(65) Prior Publication Data

US 2024/0147995 A1 May 9, 2024

(30) Foreign Application Priority Data

Oct. 25, 2022 (GB) ..................................... 2215797

(51) Int. Cl.

| | |
|---|---|
| ***A61K 38/00*** | (2006.01) |
| ***A01N 25/02*** | (2006.01) |
| ***A01N 37/46*** | (2006.01) |
| ***A01P 7/04*** | (2006.01) |
| ***C07K 7/06*** | (2006.01) |
| ***C07K 7/08*** | (2006.01) |

(52) U.S. Cl.

CPC ................ *C07K 7/06* (2013.01); *A01N 25/02* (2013.01); *A01N 37/46* (2013.01); *A01P 7/04* (2021.08); *C07K 7/08* (2013.01)

(58) Field of Classification Search

CPC ........... A01N 37/46; A01N 47/44; A01P 7/04; C07K 7/06; C07K 7/08

See application file for complete search history.

(56) References Cited

U.S. PATENT DOCUMENTS

| | | | |
|---|---|---|---|
| 5,837,218 | A | 11/1998 | Peers |
| 6,087,165 | A | 7/2000 | Raina et al. |
| 6,358,927 | B1 | 3/2002 | Altstein |
| 6,849,714 | B1 | 2/2005 | Bridon et al. |
| 7,056,942 | B2 | 6/2006 | Hildesheim et al. |
| 7,256,253 | B2 | 8/2007 | Bridon et al. |
| 7,569,748 | B2 | 8/2009 | Ensign |
| 7,605,274 | B2 | 10/2009 | Hildesheim et al. |
| 11,744,250 | B2 | 9/2023 | Bowen |
| 12,139,556 | B2 | 11/2024 | Dow et al. |
| 2003/0180297 | A1 | 9/2003 | Lowery et al. |
| 2005/0208558 | A1 | 9/2005 | Venter et al. |
| 2009/0175821 | A1 | 7/2009 | Bridon et al. |
| 2011/0263504 | A1 | 10/2011 | Cerami |
| 2016/0355556 | A1 | 12/2016 | Schwarz |
| 2019/0246647 | A1 | 8/2019 | Martinez |
| 2022/0039395 | A1 | 2/2022 | Alford et al. |
| 2022/0143214 | A1 | 5/2022 | Deverman et al. |
| 2022/0403007 | A1 | 12/2022 | Nguyen et al. |
| 2023/0309566 | A1 | 10/2023 | Choi et al. |
| 2024/0150400 | A1 | 5/2024 | Dow et al. |
| 2024/0150401 | A1 | 5/2024 | Dow et al. |
| 2024/0373849 | A1 | 11/2024 | Davies et al. |

FOREIGN PATENT DOCUMENTS

| | | | | | |
|---|---|---|---|---|---|
| CN | 104946673 | A | | 9/2015 | |
| CN | 112851760 | A | * | 5/2021 | ............. A01N 47/44 |
| CN | 121181655 | A | | 12/2025 | |
| JP | H04208300 | A | | 7/1992 | |
| JP | 2010168384 | A | | 8/2010 | |
| JP | 2011051916 | A | | 3/2011 | |
| KR | 2017 0101359 | A | | 6/2017 | |
| TR | 201700265 | A2 | | 11/2018 | |
| TR | 201902643 | A2 | | 9/2020 | |
| WO | 1995029191 | A1 | | 4/1995 | |
| WO | 199524423 | | | 9/1995 | |
| WO | 1999063082 | A2 | | 12/1999 | |
| WO | 2003066080 | A1 | | 8/2003 | |
| WO | 2009071672 | A1 | | 6/2009 | |
| WO | 2014020129 | A2 | | 2/2014 | |
| WO | 2015052701 | A1 | | 4/2015 | |
| WO | 2016153453 | A1 | | 9/2016 | |
| WO | 2016172722 | A1 | | 10/2016 | |
| WO | WO-2020115076 | A2 | * | 6/2020 | ....... C07K 14/43563 |
| WO | 2020160337 | A1 | | 8/2020 | |
| WO | 2021245429 | A1 | | 12/2021 | |
| WO | 2022251647 | A | | 12/2022 | |
| WO | 2023099922 | A1 | | 6/2023 | |
| WO | 2024089405 | A2 | | 5/2024 | |
| WO | 2025088318 | A1 | | 5/2025 | |
| WO | 2025088319 | A1 | | 5/2025 | |

(Continued)

OTHER PUBLICATIONS

Translation of CN112851760A provided by espacenet (Year: 2021).*

Smithsonian accessed on May 30, 2024 at https://www.si.edu/spotlight/buginfo/bugnos (Year: 1996).*

Nachman Ronald—Insect GPCRs and development of mimetic analogs of the insect kinin, pyrokinin-like and sulfakinin neuropeptide classes as pest management tools. Book chapter, 2018. USDA. https://www.ars.usda.gov/research/publications/publication/?seqNo115=355830 (Year: 2018).*

Zdobinsky et al. (Chem. Bio. Chem. 2009, 10, 2644-2653). Structures of Micelle-Bound Selected Insect Neuropeptidesand Analogues: Implications for Receptor Selection (Year: 2009).*

Howarth et al. Journal of Insect Physiology 48 (2002) 75-82. Structure-activity relationship of contractile effects induced by helicokinins in the isolated gut of the lepidopteran caterpillar *Spodoptera frugiperda* (Year: 2002).*

(Continued)

*Primary Examiner* — Lianko G Garyu
*Assistant Examiner* — Mercy H Sabila
(74) *Attorney, Agent, or Firm* — Nixon Peabody LLP

(57) ABSTRACT

The present invention relates to natural or natural-like analogues of insect kinin neuropeptide [Hy]-KVKFSAWG-[$NH_2$] (SEQ ID NO:2) having activity against insects, for example hemipteran, dipteran, lepidopteran and/or blattodean insects, such as aphids, moths and fruit flies, and their use as insect control agents (e.g. insecticides) and plant protection agents.

9 Claims, 8 Drawing Sheets

Specification includes a Sequence Listing.

(56) References Cited

FOREIGN PATENT DOCUMENTS

WO 2025088320 A1 5/2025

OTHER PUBLICATIONS

Howarth et al. (Journal of Insect Physiology 48 (2002) 75-82). (Year: 2002).*
Nachman, Mimetic analogs of pyrokinin neuropeptides for pest insect management, American Chemical Society, ACS Symposium Series, Washington D.C., 2014, pp. 83-94 (Year: 2014).
Alstein, Novel insect control agents based on neuropeptide antagonists, Journal of Molecular Neuroscience, 2004, 22:147-157.
Teal et al., Development of amphiphylic mimics of insect neuropeptides for pest control, Ann NY Acad Sci, 1999:897:348-60 (Year: 1999).
Martins et al., Germline transformation of the diamondback moth, *Plutella xylostella* L., using the piggyBac transposable element, Insect Molecular Biology (2012) 21(4):414-421.
Encyclopaedia Britannica, List of insects (retrieved from https://www.britannica.com/topic/list-of-insects-2073946 on Jan. 29, 2018, 20 pages) (Year: 2018).
Wegener et al, Molecular evolution of neuropeptides in the genus *Drosophila*, Genome Biology, 2008, 9, pp. R131-1-R-131-19.
Audsley et al, Genomic and peptidomic analyses of the neuropeptides from the emerging pest, *Drosophila suzukii*, Peptides, 2015, 68, pp. 33-42.
Chen et al, Synergy evaluation by a pathway-pathway interaction network; a new way to predict drug combination, Mol. BioSyst., 2016, 12, pp. 614-623.
U.S. Appl. No. 18/491,957, filed Oct. 23, 2023, Dow et al., Insect Neuropeptides 1.
U.S. Appl. No. 18/491,990, filed Oct. 23, 2023, Dow et al., Insect Neuropeptides 2.
U.S. Appl. No. 18/492,006, filed Oct. 23, 2023, Dow et al., Insect Neuropeptides 3.
U.S. Appl. No. 18/492,058, filed Oct. 23, 2023, Dow et al., Insect Neuropeptides 4.
U.S. Appl. No. 18/492,050, filed Oct. 23, 2023, Dow et al., Insect Neuropeptides 8.
U.S. Appl. No. 18/492,076, filed Oct. 23, 2023, Dow et al., Insect Neuropeptides 9.
European Search Report for EP 23205113 dated Feb. 19, 2024, 15 pages.
Scherkenbeck et al., Insect neuropeptides: Structures, chemical modifications and potential for insect control, Bioorganic & Medical Chemistry, 2009, Vo. 17(12) pp. 4071-4084.
Lee et al., Molecular characterization of pheromone biosynthesis activating neuropeptide from the diamondback moth, *Plutella xylostella*, Peptides, 2005, vol. 26(12), pp. 2404-2411.
European Search Report for EP 23205120 dated Feb. 19, 2024, 15 pages.
European Search Report for EP 23205118 dated Feb. 19, 2024, 5 pages.
European Search Report for EP 23205115 dated Feb. 19, 2024, 8 pages.
Nachman et al., Biostable and PEG polymer-conjugated insect pyrokinin analogs demonstrate antifeedant activity and induce high mortality in the pea aphid *Acyrthosiphon pisum*, Peptides, 2011, vol. 34(1), pp. 266-273.
Huybrechts et al., Neuropeptide and neurohormone precursors in the pea aphid, *Acyrthosiphon pisum: Acyrthosiphon pisum* neuropeptides, Insect Molecular Biology, 2010, vol. 19, pp. 87-95.
NCBI database record: putative uncharacterized protein DDB_G0274435 [*Myzus persicae*], Aug. 11, 2017, NCBI Reference Sequence: XP_022178913.1, https://www.ncbi.nlm.nih.gov/protein/XP_022178913.1?report=genbank&log$=prottop&blast_rank=1&RID=YXVD8V43016.
NCBI database record: serine/threonine-protein kinase STE20-like isoform X2 [Myzus persicae], Aug. 11, 2017, NCBI Reference Sequence: XP_022163650.1, https://www.ncbi.nlm.nih.gov/protein/XP_022163650.1?report=genbank&log$=prottop&blast_rank=2&RID=YXVE86PW016.
GB Search Report for GB2215797.8 dated May 30, 2023, 2 pages.
Smagghe et al., Antifeedant activity and high mortality in the pea aphid *Acyrthosiphon pisum* (*Hemiptera: Aphidae*) induced by biostable insect kinin analogs, Peptides 31, 2010, pp. 498-505.
Al-Dawsary et al., Quantitative Changes in Protein and Cholesterol in Haemolymph of the Red Palm Weevil *Rhynchophorus ferrugineus* after Treatment Leucokininll, Journal of Agricultural Sci and Technology , 2013, pp. 140-145.
Nachman et al., A C-terminal aldehyde analog of the insect kinins inhibits diuresis in the housefly, Peptides, vol. 28(1), 2007, pp. 146-152.
Nachman et al., Active diuretic prptidomimetic insect kinin analogs that contain B-turn mimetic motif 4-aminopyroglutamate and lack native peptide bonds, Peptides, vol. 34(1), 2012, pp. 262-265.
Communication relating to the results of the partial international search for PCT/GB2023/052767, dated Mar. 4, 2024, 20 pages.
Coast et al., Diuretic and myotropic activities of N-terminal truncated analogs of *Musca domestica* kinin neuropeptide, Peptides 23, 2002, vol. 23(4), pp. 701-708.
Nachman et al., Enhanced in vivo activity of peptidase-resistant analogs of the insect kinin neuropeptide family, Peptides 23, 2002, pp. 735-745.
Roberts et al., Consensus chemistry and R-turn conformation of the active core of the insect kinin neuropeptide family, Chemistry & Biology, 1997, vol. 4(2), pp. 105-117.
Howarth et al., Structure-activity relationship of contractile effects induced by helicokinins in the isolated gut of the lepidopteran caterpillar *Spodoptera frugiperda*, Journal of Insect Physiology, 2002, vol. 48(1), pp. 75-82.
Leonard et al., Structure-activity Relationships of Cysteine-Lacking Pentapeptide Derivatives That Inhibit ras Farnesyltransferase, Journal of Medicinal Chemistry, 1997, vol. 40, pp. 192-200.
European Search Report for EP 23205098, dated Feb. 15, 2024, 14 pages.
Hayes et al., Leucokinins, A New Family of Ion Transport Stimulators and Inhibitors in Insect Malpighian Tubules, Life Sciences, 1989, vol. 44(18), pp. 1259-1266.
European Search Report for EP 23205100, dated Feb. 15, 2024.
Blackburn et al., The isolation and identification of three diuretic kinins from the abdominal ventral nerve cord of adult *Helicoverpa zea*, Journal of Insect Physiology, 1995, vol. 41(8), pp. 723-730.
European Search Report for EP 23205099, dated Feb. 14, 2024, 11 pages.
Coast et al., Target Organ Specificity of Major Neuropeptide Stimulants in Locust Excretory Systems, The Journal of Experimenal Biology 202, 1999, pp. 3195-3203.
Coast, The Influence of Neuropeptides on the Spontaneous Writhing Movements of Locust Malpighian Tubules, Annals of the New York Academy of Sciences 839.1, 1998, pp. 346-347.
Coast, The influence of neuropeptides on Malpighian tubule writhing and its significance for excretion, Peptides, 1998, vol. 19(3) pp. 469-480.
Predel et al., Isolation and structural elucidation of eight kinins from the retrocerebral complex of the American cockroach, *Periplaneta americana*, Regulatory Peptides, 1997, vol. 71, pp. 199-205.
Seinsche et al., Effect of helicokinins and ACE inhibitors on water balance and development of *Heliothis virescens* larvae, Journal of Insect Physiology, 2000, vol. 46, pp. 1423-1431.
Coast, Synergism between diuretic peptides controlling ion and fluid transport in insect malpighian tubules, Regulatory Peptides, 1995, vol. 57, pp. 283-296.
Schoofs et al., Locustakinin, a novel myotropic peptide from Locusta migratoria, isolation, primary structure and synthesis, Regulatory Peptides, 1992, vol. 37, pp. 49-27.
Umetsu et al., Substrate Specificity of Aminopeptidase from the Mid-gut Gland of the Scallop (*Patinopecten yessoensis*), Bioscience, biotechnology, and biochemistry, 2004, vol. 68(4), pp. 945-947.

(56) References Cited

OTHER PUBLICATIONS

Caers et al., Peptidomics of neuropeptidergic tissues of the tsetse fly *Glossina morsitans morsitans*, Journal of the American society for mass spectrometry, 2015, vol. 26(12), pp. 2024-2038.
Caers, et al., Structure-activity studies of *Drosophila* adipokinetic hormone (AKH) by a cellular expression system of dipteran AKH receptors, General and comparative endocrinology, 2012, vol. 177(3), pp. 332-337.
Schwarz et al., Hugin+ neurons provide a link between sleep homeostat and circadian clock neuron, Proceedings of the National Academy of Sciences, 2021, vol. 118(47), pp. 1-10.
Oh et al., Periphery signals generated by Piezo-mediated stomach stretch and Neuromedin-mediated glucose load regulate the *Drosophila* brain nutrient sensor, Neuron, 2021, vol. 109(12), pp. 1979-1995.
Mizuno et al., A population of neurons that produce hugin and express the diuretic hormone 44 receptor gene projects to the corpora allata in *Drosophila melanogaster*, Development, Growth & Differentiation, 2021, vol. 63(4-5), pp. 249-261.
Martelli et al., SIFamide translates hunger signals into appetitive and feeding behavior in *Drosophila*, Cell reports, 2017, vol. 20(2), pp. 464-478.
Audsley et al., Neuropeptides associated with the central nervous system of the cabbage root fly, *Delia radicum* (L), Peptides, 2011, vol. 32(3), pp. 434-440.
Gäde et al., Isolation and structure of a novel charged member of the red-pigment-concentrating hormone-adipokinetic hormone family of peptides isolated from the corpora cardiaca of the blowfly *Phormia terraenovae* (*Diptera*), Biochemical journal, 1990, vol. 269(2), pp. 309-313.
Zoephel, et al., Peptidomics of the agriculturally damaging larval stage of the cabbage root fly *Delia radicum* (*Diptera: Anthomyiidae*), Plos One, 2012, vol. 7(7), pp. e41543.
NCBI database record: hypothetical protein KR222_006153, partial [Zaprionus bogoriensis], GenBank: KAH8416674.1, Dec. 17, 2021, https://www.ncbi.nlm.nih.gov/protein/KAH8416674.1.
NCBI database record: putative uncharacterized protein DDB_G0274435 [Myzus persicae], NCBI Reference Sequence: XP_022178913.1, Aug. 11, 2017, https://www.ncbi.nlm.nih.gov/protein/XP_022178913.1?report=genbank&log$=prottop&blast_rank=1&RID=YXVD8V43016.
NCBI database record: serine/threonine-protein kinase STE20-like isoform X2 [Myzus persicae], NCBI Reference Sequence: XP_022163650.1, Aug. 11, 2017, https://www.ncbi.nlm.nih.gov/protein/XP_022163650.1?report=genbank&log$=prottop&blast_rank=2&RID=YXVE86PW016.
Meng et al., The *Drosophila* hugin gene codes for myostimulatory and ecdysis-modifying neuropeptides, Mechanisms of development, 2002, vol. 117(1-2), pp. 5-13.
European Search Report for EP 23205097 dated Feb. 19, 2024, 8 pages.
Kölisch et al., Structure elucidation and biological activity of an unusual adipokinetic hormone from corpora cardiaca of the butterfly, *Vanessa cardui*, Eur. J. Biochem., 2000, vol. 267(17), pp. 5502-5508.
ISR/WO for PCT/GB2022/053082 mailed Mar. 3, 2023, 16 pages.
Garczynski et al., Neuropeptides and peptide hormones identified in codling moth, *Cydia pomonella* (*Lepidoptera: Tortricidae*), Arch. Insect Biochem. Physiol.2019, 101(4) 19 pages.
Sturm et al., Serine phosphorylation of CAPA pyrokinin in cockroaches—a taxon-specific posttranslational modification, Peptides, 2014, 57:52-58.
Jiang et al., Functional characterization of five different PRXamide receptors of the red flour beetle *Tribolium castaneum* with peptidomimetics and identification of agonists and antagonists, Peptides, 2015, 68:246-252.
Alford et al., Assessment of neuropeptide binding sites and the impact of biostable kinin and CAP2b analogue treatment on aphid (*Myzus persicae* and *Macrosiphum rosae*) stress tolerance, Pest Management Science, 2019, vol. 75(6).
Alford et al., Desiccation, thermal stress and associated mortality in *Drosophila* fruit flies induced by neuropeptide analogue treatment, Journal of Pest Science, 2019, vol. 92, pp. 1123-1137.
Zhang et al., Disruption of insect diapause using agonists and an antagonist of diapause hormone, Proceedings of the National Academy of Sciences, 2011, vol. 108(41), pp. 16922-16926.
Shi et al., Efficacy and biosafety assessment of neuropeptide CAPA analogues against the peach-potato aphid (*Myzus persicae*), Insect Science, 2021, pp. 1-10.
Gui et al., Assessment of insecticidal effects and selectivity of CAPA-PK peptide analogues against the peach-potato aphid and four beneficial insects following topical exposure, Pest Management Science, 2020, vol. 76(10), pp. 3451-3458.
Nachman et al., Structure-activity relationships for in vitro diuretic activity of CAP2b in the housefly, Peptides 28, 2007, vol. 28(1), pp. 58-61.
International Search Report and Written Opinion for PCT/GB2021/051401 dated Oct. 18, 2021, 18 pages.
Coast et al., New aspects of insect diuretic hormone function, XII International Congress of Comparative Endocrinology, 1997, pp. 107-113.
U.S. Appl. No. 18/007,513, filed Dec. 1, 2022, Davies et al., Insect Neuropeptide Analogues.
U.S. Appl. No. 18/714,954, filed May 30, 2024, Davies et al., Insect Neuropeptide Analogues.
NCBI database record: hypothetical protein KR222_006153, partial [Zaprionus bogoriensis], GenBank: KAH8416674.1, https://www.ncbi.nlm.nih.gov/protein/KAH8416674.1.
Köllisch et al., Vanessa cardui adipokinetic hormone (Vanca-AKH) in butterflies and a moth, Comparative Biochemistry and Physiology Part A: Molecular & Integrative Physiology, 2003, vol. 135(2), pp. 303-308.
NCBI database record: pyrokinin [*Drosophila suzukii*], GenBank: APU93592.1, https://www.ncbi.nlm.nig.gov/protein/APU93592.1.
Umadevi Dissertation, Biochemical and molecular characterization of an adipokinetic neuropeptide from the mango leaf webber, *Orthaga Exvinacea hampson* (*pyralidae: lepidoptera*) Univ Calicut India 2012, 185 pages.
Enclyclpedia Britannica (retrieved from https://www.britannica.com/print/article/264344 on Jul. 18, 2024, 19 pages, 2024.
NCBI Reference Sequence: XP_022163633.1, 2017, 2 pages (cumulative).
Smithsonian accessed on May 30, 2024 at https://www.si.edu/spotlight/buginfo/bugnos, 1996, 8 pages.
Chowanski et al., Synthetic Insecticides—is There an Alternative?, Pol. J. Environ. Stud., 2014, vol. 23(2), pp. 291-302.
Predel et al., Comparative peptidomics of four related hemipteran species: *Pyrokinins, myosuppressin, corazonin*, adipokinetic hormone, sNPF, and *periviscerokinins*, Peptides 29, 2008, pp. 162-167.
Lalitha Bhai, Hemiptera: Morphology and Phylogeny, Entomol Ornithol Herpetol, 2002, p. 1.
Duve et al., [Hyp3] Met-callatostatin. Identification and biological properties of a novel neuropeptide from the blowfly *Calliphora vomitoria*, Journal of Biological Chemistry 269.33, 1994, pp. 21059-21066.
Gäde et al., Unique translational modification of an invertebrate neuropeptide: a phosphorylated member of the adipokinetic hormone peptide family, Biochemical Journal 393.3, 2006, pp. 705-713.
Munte et al., C-mannsylation in the hypertrehalosaemic hormone from the stick insect *Carausius morosus*, The FEBS Journal, 2008, pp. 1163-1173.
Nachman et al., Leucosulfakinin, a sulfated insect neuropeptide with homology to gastrin and cholecystokinin, Science 234.4772, 1986, pp. 71-73.
Gäde et al., An invertebrate [hydroxyproline]-modified neuropeptide: Further evidence for a close evolutionary relationship between insect adipokinetic hormone and mammalian gonadotropin hormone family, Biochemical and Biophysical Research Communications 414.3, 2011, pp. 592-597.
GB Search Report for GB2208466.9 dated Nov. 25, 2022, 5 pages.

(56) References Cited

OTHER PUBLICATIONS

Kodrik et al., Adipokinetic hormone (Pyrap-AKH) enhances the effect of a pyrethroid insecticide against the firebug *Pyrrhocoris apterus*, Pest Management Science: formerly Pesticide Science 66.4, 2010, pp. 425-431.
Kodrik et al., The effect of insecticide on adipokinetic hormone titre in the insect body, Pest Management Science: formerly Pesticide Science 61.11, 2005, pp. 1077-1082.
Mugumbate et al., Open conformation of adipokinetic hormone receptor from the malaria mosquito facilitates hormone binding, Peptides 32.3, 2011, pp. 553-559.
Rahman et al, Neuropeptidomics of the Australian sheep blowfly *Lucilia cuprina* (Wiedemann) and related Diptera, Peptides 41, 2013, pp. 31-37.
Ivana, et al., Hormonal enhancement of insecticide efficacy in Tribolium castaneum: oxidative stress and metabolic aspects, Comparative Biochemistry and Physiology Part C: Toxicology & Pharmacology 170, 2015, pp. 19-27.
GB Search Report for GB2316140.9 dated Apr. 16, 2024, 4 pages.
GB Search Report for GB2316141.7 dated Apr. 16, 2024, 4 pages.
Ierusalimsky Victor et al, Neuropeptides of *Drosophila* related to molluscan neuropeptides: Dependence of the immunoreactivity pattern on the ontogenetic stage and functional state, Brain Research, 2007, vol. 1152, pp. 32-41.
Xiong Caixing et al., Myotropic Activities of Tick Pyrokinin Neuropeptides and Analog in Feeding Tissues of Hard Ticks (*Ixodidae*), Frontiers in Physiology, 2022, vol. 12, pp. 1-10.
European Search Report for EP 23205095 dated Mar. 26, 2024, 15 pages.
Anonymous, Suspension Concentrates, Stepan Agricultural Solutions, 2021, 4 pages.
Boerjan et al., Dispersion of peptides in vegetable oil as simple slow release formula for both injection and oral uptake in insects: A case study with [His7]-corazonin in an albino Locusta migratoria deficient in corazonin, Peptides 32, 2011, pp. 1536-1539.
Fonagy, Insect Neuropeptides and their Potential Application for Pest Control, Acta Phytopathologica et Entomologica Hungarica 41, 2006, pp. 137-152.
Batta, Invert emulsion: Method of preparation and application as proper formulation of entomopathogenic fungi, MethodsX 3, 2016, pp. 119-127.
Kola et al., Key enzymes and proteins of crop insects as candidate for RNAi based gene silencing, Frontiers in Physiology, 2015, vol. 6(119), pp. 1-15.
Anonymopus, Atplus UEP-100; Formulating for Delivery; Croda, 2015, 16 pages.
Kean, Laura, et al., Two nitridergic peptides are encoded by the gene capability in *Drosophila melanogaster*, American Journal of Physiology-Regulatory, Integrative and Comparative Physiology 282.5, 2002, pp. R1297-R1307.
Nachman, Ronald J., et al., MALDI-TOF/TOF Mass Spectrometric Assignment of Leu/lle in PVK-CAP2b Neuropeptides From Single Neurohemal Organ Preparations of Four Flies, Pestycydy, 2005, pp. 49-53.
Terhzaz et al., Insect capa neuropeptides impact desiccation and cold tolerance, Proceedings of the National Academy of Sciences, vol. 112(9), 2015, pp. 2882-2887.
Terhzaz et al., Mechanism and function of *Drosophila* capa GPCR: a desiccation stress-responsive receptor with functional homology to human neuromedinU receptor, PloS one, 2012, vol. 7(1), pp. 1-13.
Xu, Gang, et al., Identification and expression profiles of neuropeptides and their G protein-coupled receptors in the rice stem borer *Chilo suppressalis*, Scientific Reports 6.1, 2016, pp. 1-15.
Christie, In silico analyses of peptide paracrines/hormones in Aphidoidea, General and Comparative Endocrinology, 2008, vol. 159(1), pp. 67-79.
Jiang et al., Molecular cloning and functional characterization of the diapause hormone receptor in the corn earworm *Helicoverpa zea*, Peptides, 2014, vol. 53, pp. 243-249.
Bowie et al., Deciphering the Message in Protein Sequences: Tolerance to Amino Acid Substitutions, Science, 1990, vol. 247, pp. 1306-1310.
Burgess et al., Possible Dissociation of the Heparin-binding and Mitogenic Activities of Hepartin-binding (Acidic Fibroblast) Growth Factor-1 from Its Receptor-binding Activities by Site-directed Mutagenesis of a Single Lysine Residue, The Journal of Cell Biology, 1990, vol. 111, pp. 2129-2138.
Lazar et al., Transforming Growth Factor a: Mutation of Aspartic Acid 47 and Leucine 48 Results in Different Biological Activities, Molecular and Cellular Biology, 1988, vol. 8(3), pp. 1247-1252.
Choi, Pheromone Biosynthesis Activating Neuropeptide (PBAN) in Insects, Korean Journal of Applied Entomology, 2022, vol. 61(1), pp. 15-28.
Anonymous, Concentrated Emulsions fact sheet, Stepan Agricultural Solutions, 2022, 4 pages.
International Search Report and Written Opinion for PCT/GB2023/052767 dated Apr. 25, 2025, 22 pages.
European Search Report for EP 23801502, dated Apr. 10, 2026, 3 pages.
S. Ons et al., Neuropeptide precursor gene discovery in the Chagas disease vector Rhodnius prolixus, Insect Molecular Biology, 2011, vol. 20(1), pp. 29-44.
Taneja-Bageshwar et al., Identification of selective and non-selective, biostable B-amino acid agonists of recombinant insent kinin receptors from the southers cattle tick *Boophilus microplus* and mosquito *Aedes aegypti*, Peptides 29, 2008, pp. 302-309.
U.S. Appl. No. 19/580,380, filed Apr. 21, 2026, Dow et al., Insect Neuropeptide Analogues.
International Search Report and Written Opinion for PCT/GB2024/052712, dated Mar. 14, 2025, 9 pages.
U.S. Appl. No. 19/580,383, filed Apr. 21, 2026, Dow et al., Insect Neuropeptide Analogues.
International Search Report and Written Opinion for PCT/GB2024/052714, dated Feb. 19, 2025, 13 pages.
U.S. Appl. No. 19/580,389, filed Apr. 21, 2026, Dow et al., Insect Neuropeptide Analogues.
International Search Report and Written Opinion for PCT/GB2024/052711, dated Apr. 9, 2025, 18 pages.
Feng et al., Design, Synthesis, and Aphicidal Activity of Novel Insect Neuropeptide Kinin Receptor Antagonists, Targeting the Ser2 Ligand Position, The Journal of Agricultural and Food Chemistry, 2025, pp. 25505-25514.
Orchard et al., Functional characterization of the kinin receptor in the Chagas disease vector Rhodnius prolixus; activity of native kinins and potent biostable Aib-containing insect kinin analogs, Peptides 172 (2024) 171135, 7 pages.
Konopinska et al., Insect neuropeptides as agents for pest control: potential and challenges, Biological Research (2026) 59:6, 20 pages.
Zhang et al., Peptides, new tools for plant protection in eco-agriculture, Advanced Agrochem 2 (2023) 58-78, 21 pages.

* cited by examiner

KININ VS *PLUTELLA XYLOSTELLA*
SB-P-70

INSECT NEUROPEPTIDES 5

CROSS-REFERENCE TO RELATED APPLICATIONS

This application includes a claim of priority under 35 U.S.C. § 119(a) to United Kingdom patent application No. GB2215797.8, filed Oct. 25, 2022, the entirety of which is hereby incorporated by reference.

REFERENCE TO SEQUENCE LISTING

This application contains a Sequence Listing submitted as a computer readable form named "SB-P-70-P365409EP-US_v3.xml", having a size in bytes of 24,397 bytes, and created on Oct. 13, 2023 ("production date"). The information contained in this computer readable form is hereby incorporated by reference in its entirety.

FIELD OF THE INVENTION

The present invention relates to natural or natural-like analogues of insect kinin neuropeptides having activity against insects, for example hemipteran, dipteran, lepidopteran and/or blattodean insects, such as aphids, moths and fruit flies, and their use as insect control agents (e.g. insecticides) and plant protection agents.

BACKGROUND

With a global dependence on broad-spectrum insecticides, the damaging effects of which are well documented, there is increasing need for the development of greener, target-specific insecticides with which to protect valuable crop plants. The development and employment of neuropeptides, and their synthetic analogues offers a promising avenue in the drive for greener and target-specific insecticidal agents.

Within insects, neuropeptides are regulatory peptides with functional roles in growth and development, behaviour and reproduction, metabolism and homeostasis, and muscle movement. Insect neuropeptide families are large and include the insect kinins and CAPA (CAPA, CAP2b, CAPA3) neuropeptides, AKH peptides, and the pyrokinin peptides.

Due to their high specificity, insect neuropeptides and their cognate receptors (G-protein coupled receptors, GPCRs) may be developed towards insecticidal agents to selectively reduce the fitness of target pest insects, whilst minimising detrimental environmental impacts, and minimising harm to other non-target species such as pollinators, which have seen dangerously declining population numbers due to pesticide/insecticide use.

There have been attempts in the art to provided modified synthetic analogues of such insect neuropeptides for use as targeted insecticides, which show promising results. However, whilst desirable and effective, these modified peptides may be challenging to bring to market in many territories in which the use of such modified peptides is heavily regulated.

The present invention aims to solve one or more of the above-mentioned problems, and provides novel natural kinin neuropeptides, and natural-like variants or analogues thereof for use as insect control agents and plant protection agents.

SUMMARY OF THE INVENTION

The inventors have discovered new kinin peptides, and natural-like variants or analogues thereof, having insecticidal activity against insects such as hemipteran, dipteran, lepidopteran and/or blattodean insects, and so potentially finding use as pest control agents or insecticides, while having little or no effect against important pollinator species such as bees.

Thus, in a first aspect, the invention provides an insecticidal compound having the formula (I) below, or a salt or solvate thereof:

$$R^1—Y^1—Z—Y^2—R^2 \quad (I)$$

wherein:

$R^1$ is hydrogen (which may be designated "H-" or "Hy-"), $C_{1-4}$alkyl (e.g. methyl, ethyl, propyl, butyl), formyl, acyl, fatty acyl, a sugar moiety, phosphate or sulphate, or $R^1$ is a pyroglutamate group of the formula:

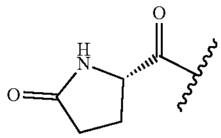
;

and any alkyl, formyl, acyl or fatty acyl may optionally be substituted with one or more groups selected from oxo or $C_{1-6}$alkyl or a sugar moiety, phosphate or sulphate;

$Y^1$ is absent or is a peptide comprising from 1 to 2 amino acids;

Z is a peptide according to formula

KVKFSAWG (SEQ ID NO:1);

$Y^2$ is absent or is a peptide comprising from 1 to 2 amino acids;

$R^2$ is $NH_2$, $NR^{2a}H$, $NR^{2a}R^{2b}$, OH or $OR^{2a}$; wherein each of $R^{2a}$ and $R^{2b}$ if present are independently $C_{1-6}$-alkyl (e.g. methyl, ethyl, propyl, butyl, pentyl or hexyl).

In another aspect, there is provided a composition comprising a compound as defined herein, or a salt thereof, in admixture with one or more solvents, carriers, diluents, adjuvants, preservatives, dispersants, emulsifying agents, or synergists. Suitably, the composition is an agricultural composition, an insect control composition or plant protection composition.

In another aspect, there is provided the use of a compound as defined herein, or a salt thereof, or a composition as defined herein, as an insect control agent. The use may be as an insecticide against insects that encode the kinin peptide. The use may be as an insecticide against hemipteran, dipteran, lepidopteran and/or blattodean insects, preferably hemipteran, dipteran and/or lepidopteran insects, most preferably lepidopteran insects such as moths.

In another aspect, there is provided a method of increasing insect mortality, the method comprising contacting an insect population with a compound as defined herein, or a salt thereof, or a composition as defined herein. Suitably, the insect is an insect that encodes the kinin peptide, such as hemipteran, dipteran, lepidopteran and/or blattodean insects, preferably hemipteran, dipteran and/or lepidopteran insects, most preferably lepidopteran insects such as moths.

In another aspect, there is provided a method of increasing hemipteran, dipteran, lepidopteran and/or blattodean insect mortality, the method comprising contacting a hemipteran, dipteran, lepidopteran and/or blattodean insect population with a compound as defined herein, or a salt thereof, or a composition as defined herein. Preferably the insect is a lepidopteran insect such as moths.

In another aspect, there is provided the use of a compound as defined herein, or a salt thereof, or a composition as defined herein, as a plant protection agent, for protecting a plant against insects that encode the kinin peptide. Preferably the insect is a lepidopteran insect such as moths.

In another aspect, there is provided the use of a compound as defined herein, or a salt thereof, or a composition as defined herein, as a plant protection agent, for protecting a plant against hemipteran, dipteran, lepidopteran and/or blattodean insects, preferably hemipteran, dipteran and/or lepidopteran insects, most preferably lepidopteran insects such as moths.

In another aspect, there is provided a method of inhibiting infestation of a plant by insects that encode the kinin peptide, the method comprising contacting the plant with a compound as defined herein, or a salt thereof, or a composition as defined herein. Suitably, the compound or composition is applied to the plant while the plant is free or substantially free of insects that encode the kinin peptide.

In another aspect, there is provided a method of inhibiting infestation of a plant by hemipteran, dipteran, blattodean and/or lepidopteran insects comprising contacting the plant with a compound as defined herein, or a salt thereof, or a composition as defined herein. Suitably, the compound or composition is applied to the plant while the plant is free or substantially free of hemipteran, dipteran, lepidopteran and/or blattodean insects. Preferably the insects are selected from hemipteran, dipteran and/or lepidopteran insects, most preferably lepidopteran insects such as moths.

In another aspect, there is provided a method of reducing infestation of a plant by insects that encode the kinin peptide, or of reducing load of insects that encode the kinin peptide on a plant, the method comprising contacting the plant with a compound as defined herein, or a salt thereof, or a composition as defined herein.

In another aspect, there is provided a method of reducing hemipteran, dipteran, lepidopteran and/or blattodean insect infestation of a plant, or of reducing hemipteran, dipteran, lepidopteran and/or blattodean insect load on a plant, the method comprising contacting the plant with a compound as defined herein, or a salt thereof, or a composition as defined herein. Preferably the insects are selected from hemipteran, dipteran and/or lepidopteran insects, most preferably lepidopteran insects such as moths. In one embodiment, the compounds, compositions, and agents of the invention suitably have activity against the moth species *Plutella xylostella*. In one embodiment, the compounds, compositions, and agents of the invention suitably have activity against the moth species *Spodoptera frugiperda*.

Suitable insects which encode the kinin peptide include hemipteran, dipteran, lepidopteran and/or blattodean insects, preferably hemipteran, dipteran and/or lepidopteran insects. In a preferred embodiment, the insects which encode the kinin peptide are lepidopteran insects such as moths.

In another aspect, there is provided a method of producing an insecticidal compound according to the first aspect, the method comprising:

(a) chemically synthesising the insecticidal compound of formula (I) or a precursor thereof.

In one embodiment, the chemical synthesis comprises the method described in the examples. In one embodiment, the chemical synthesis comprises the method and steps shown in FIG. 2.

Further features of the aspects and embodiments of the invention will now be defined under the following headed sections. Any feature in any section may be combine with any aspect of embodiment in any workable combination.

DETAILED DESCRIPTION OF THE INVENTION

Definitions

Throughout the present description and claims the conventional three-letter and one-letter codes for naturally occurring amino acids are used, i.e. A (Ala), G (Gly), L (Leu), I (Ile), V (Val), F (Phe), W (Trp), S (Ser), T (Thr), Y (Tyr), N (Asn), Q (Gin), D (Asp), E (Glu), K (Lys), R (Arg), H (His), M (Met), C (Cys) and P (Pro).

'Amino acid' as referred to herein may refer to a naturally occurring amino acid or any other amino acid including synthetic amino acids, and non-proteinogenic amino acids. By "naturally occurring" in this context is meant the 20 amino acids encoded by the standard genetic code, sometimes referred to as proteinogenic amino acids.

The term amino acid is short for α-amino [alpha-amino] carboxylic acid. Each molecule contains a central carbon atom, called the α-carbon, to which both an amino and a carboxyl group are attached. The remaining two bonds of the α-carbon atom are generally satisfied by a hydrogen (H) atom and the side chain, shown as R below:

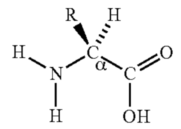

Unless otherwise specified, amino acid residues in peptides of the invention are of the L-configuration. As used herein, the terms "polypeptide", "protein", "peptide", are used interchangeably, and refer to a polymeric form of amino acids of any length, which can include coded and non-coded amino acids. As used herein, amino acid residues will be indicated as above either by their full name or according to the standard three-letter or one-letter amino acid code.

The notation $C_{x-xx}$ refers to the number of carbon atoms in a functional group. The number in the 'x' positions is the lowest number of carbon atoms and the number in the 'xx' position denotes the highest number of carbon atoms. For example, $C_{1-6}$-alkyl refers to alkyl groups as defined herein having from 1 to 6 carbon atoms.

The notation l, n or t are used herein in relation to various alkyl groups in the normal way. Specifically, the suffixes refer to the arrangement of atoms and denote straight chain ('n') or branched ('i' or 't') alkyl groups.

The term "alkyl" as used herein refers to a saturated linear or branched-chain monovalent hydrocarbon radical, wherein the alkyl radical may be optionally substituted. The number of carbon atoms in the alkyl group may be specified using the above notation, for example, when there are from 1 to 8 carbon atoms the term "$C_{1-8}$-alkyl" may be used. Examples of alkyl groups include methyl (Me, $-CH_3$), ethyl (Et, $-CH_2CH_3$), 1-propyl (n-Pr, n-propyl, $-CH_2CH_2CH_3$), 2-propyl (i-Pr, i-propyl, $-CH(CH_3)_2$), and 1-butyl (n-Bu, n-butyl, $-CH_2CH_2CH_2CH_3$).

An "alkylene," "alkenylene," or "alkynylene" group is an alkyl, alkenyl, or alkynyl group that is positioned between and serves to connect two other chemical groups. Thus, "$C_{1-6}$ alkylene" means a linear saturated divalent hydrocarbon radical of one to six carbon atoms or a branched saturated divalent hydrocarbon radical of three to six carbon atoms. Example alkylene groups include methylene $-CH_2-$), 1,1-ethylene ($-CH(CH_3)-$), 1,2-ethylene ($-CH_2CH_2-$), 1,1-propylene ($-CH(CH_2CH_3)-$), and 2,2-propylene ($-C(CH_3)_2-$).

The term "alkenyl" as used herein refers to a linear or branched-chain monovalent hydrocarbon radical with at least one site of unsaturation, i.e., a carbon-carbon double bond. The alkenyl radical may be optionally substituted, and includes radicals having "cis" and "trans" orientations, or alternatively, "E" and "Z" orientations. The number of carbon atoms in the alkenyl group may be specified using the above notation, for example, when there are from 2 to 8 carbon atoms the term "$C_{2-8}$-alkenyl" may be used. Example alkenyl groups include, but are not limited to, ethenyl ($-CH{=}CH_2$), and prop-1-enyl ($-CH{=}CHCH_3$).

In the chemical structures drawn herein, the presence of "" or "" denotes a point of attachment or a radical for example, a radical as discussed in relation to various functional groups.

The term "comprising" is used in the present description and claims, it does not exclude other elements or steps. Where an indefinite or definite article is used when referring to a singular noun e.g. "a" or "an", "the", this includes a plural of that noun unless something else is specifically stated.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier 'about' refers is itself also specifically, and preferably, disclosed.

"Plant" as used herein, means an entire plant or a part thereof, including fresh fruit, vegetables and seeds. The plant or plant part may be a live plant or part thereof. Also, the term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

"Crop" as used herein means a plant species or variety that is grown to be harvested as food, livestock fodder, fuel raw material, or for any other economic purpose. As a non-limiting example, said crops can be maize, cereals, such as wheat, rye, barley and oats, sorghum, rice, sugar beet and fodder beet, fruit, such as pome fruit (e.g. apples and pears), citrus fruit (e.g. oranges, lemons, limes, grapefruit, or mandarins), stone fruit (e.g. peaches, nectarines or plums), nuts (e.g. almonds or walnuts), soft fruit (e.g. cherries, strawberries, blackberries or raspberries), the plantain family or grapevines, leguminous crops, such as beans, lentils, peas and soya, oil crops, such as sunflower, safflower, rapeseed, canola, castor or olives, cucurbits, such as cucumbers, melons or pumpkins, fibre plants, such as cotton, flax or hemp, fuel crops, such as sugarcane, miscanthus or switchgrass, vegetables, such as potatoes, tomatoes, peppers, lettuce, spinach, onions, carrots, egg-plants, asparagus or cabbage, ornamentals, such as flowers (e.g. petunias, pelargoniums, roses, tulips, lilies, or chrysanthemums), shrubs, broadleaved trees (e.g. poplars or willows) and evergreens (e.g. conifers), grasses, such as lawn, turf or forage grass or other useful plants, such as coffee, tea, tobacco, hops, pepper, rubber or latex plants.

A "pest", as used here, is an organism that is harmful to plants, animals, humans or human concerns, and includes, but is not limited to crop pests such as insects (as later defined), household pests or insects, such as cockroaches, ants, etc., and disease vectors, such as malaria mosquitoes.

"Pest infection" or "pest disease" as used herein refers to any inflammatory condition, disease or disorder in a living organism, such as a plant, animal or human, which is caused by a pest.

"Active substance", "active ingredient" or "active principle", as used interchangeably herein, means any biological, biochemical or chemical element and its derivatives, fragments or compounds based thereon, including microorganisms, having general or specific action against harmful organisms on a subject, and in particular on insect pests of plants, parts of plants or on plant products, as they occur naturally or by manufacture, including any impurity inevitably resulting from the manufacturing process.

The terms "effective amount" and "effective dose", as used herein, mean the amount needed to achieve the desired result or results.

An "insect", as used here, is used in the broad popular sense and includes all species of the superphylum Panarthropoda (classification Systema Naturae, Brands, S.J. (comp.) 1989-2005. Systema Naturae 2000. Amsterdam, The Netherlands, [sn2000.taxonomy.nl/]), including the phyla Arthropoda, Tardigrada and Onychophora; it includes all the different phases of the life cycle, such as, but not limited to eggs, larvae, nymphs, pupae and adults. Suitable insect pests are defined elsewhere herein.

An "insecticidal compound" as used herein refers to compounds having biological activity on insects (as defined above), including but not limited to compounds capable of killing the insect, larvaecides, insect growth regulators, behaviour modifying compounds, attractants, repellents, pheromones, kairomones, allomones and entomopathogenic fungi, viruses and proteins. The insecticide exerts its biological activity preferably by the contact of the compound with the insect, without the need of being ingested by the insect. It includes not only compounds or compound formulations that are ready to use, but also precursors in an inactive form, which may be activated by outside factors. Possibly, the insecticide may be combined with materials used in conjunction, such as synergists or safeners, flavour or odour compositions. Preferably, said compound is comprised in a carrier as defined above. "Comprised in a carrier" as used herein means bound on or contained in by means such as but not limited to embedding, encapsulation and adsorption.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

Compounds of the Invention

Particular compounds of the invention include, for example, compounds of the formula (I), wherein, unless otherwise stated, each of $R^1$, $Y^1$, $Y^2$, $R^2$ and any associated substituent group has any of the meanings defined hereinbefore or in any of paragraphs (1) to (12) hereinafter:

(1) $R^1$ is selected from hydrogen, acyl or fatty acyl, or phosphate or sulphate, or $R^1$ is a pyroglutamate group of the formula:

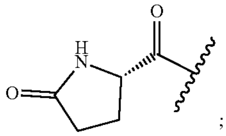 [SMILES: *C(=O)[C@@H]1CCC(=O)N1]

;

wherein acyl or fatty acyl are optionally substituted by a sugar moiety, phosphate or sulphate.

(2) $R^1$ is selected from hydrogen, formyl, acetyl (Ac), propanoyl, butanoyl, palmitoyl [palm], butyryl, cerotoyl, decanoyl, docosenoyl, dodecanoyl, eleostearoyl, heptanoyl, hexanoyl, icosanoyl, icosenoyl, lignoceroyl, linoleoyl, lipoyl, myristoleoyl, nonanoyl, octadecanoyl, ocatanoyl, palmitoleoyl, stearoyl, undecanoyl, and valeryl.

(3) $R^1$ is selected from hydrogen, acetyl or palmitoyl, or $R^1$ is a pyroglutamate group of the formula:

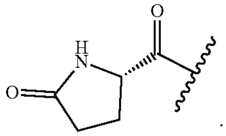 [SMILES: *C(=O)[C@@H]1CCC(=O)N1]

.

(4) $R^1$ is selected from hydrogen or palmitoyl.

(5) $R^1$ is hydrogen.

(6) $R^1$ is a pyroglutamate group of the formula:

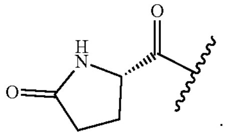 [SMILES: *C(=O)[C@@H]1CCC(=O)N1]

.

(7) $Y^1$ is absent or a peptide comprising 1 or 2 amino acid residues.

(8) $Y^1$ is absent.

(9) $Y^2$ is absent or a peptide comprising 1 or 2 amino acid residues.

(10) $Y^2$ is absent.

(11) $R^2$ is $NH_2$, $NR^{2a}H$, $NR^{2a}R^{2b}$ or OH wherein each of $R^{2a}$ and $R^{2b}$ if present is independently $C_{1-6}$-alkyl (e.g. methyl, ethyl, propyl, butyl, pentyl or hexyl).

(12) $R^2$ is $NH_2$.

Suitably, $R^1$ is as defined in any one of paragraphs (1) to (6) above. More suitably, $R^1$ is as defined in any one of paragraphs (3) to (6) above. Most suitably, $R^1$ is as defined in paragraph (4) or (5) above.

Suitably, $Y^1$ or $Y^2$ is as defined in any one of paragraphs (7) to (10) above. Most suitably, $Y^1$ or $Y^2$ is as defined in paragraphs (8) or (10) above.

Suitably, $R^2$ is as defined in paragraph (11) or (12) above. Most suitably, $R^2$ is as defined in paragraph (12) above.

In a preferred embodiment, $R^1$ is hydrogen, $Y^1$ and $Y^2$ are absent, and $R^2$ is $NH_2$.

In a preferred embodiment, $R^1$ is hydrogen, $Y^2$ is absent, $Y^1$ is one or two amino acids, and $R^2$ is $NH_2$.

In a preferred embodiment, $R^1$ is hydrogen, $Y^1$ is absent, $Y^2$ is one or two amino acids, and $R^2$ is $NH_2$.

Further Explanation of Compounds of the Invention $R^1$ and $R^2$

The terminal groups present at the N- and C-termini of the peptide backbone are designated $R^1$ and $R^2$ respectively. Thus, $R^1$ is bonded to the nitrogen atom of the N-terminal amino group of $Y^1$ and $R^2$ is bonded to the C-terminal carbonyl carbon atom of $Y^2$.

The compounds of the invention may include further functionalisation, suitably at the N or C terminus. Suitably, the compounds may be functionalised to increase cuticle permeability or to increase stability. Suitably, the compound may be functionalised with an aromatic, aliphatic or lipophilic group. Suitably therefore, $R^1$ may be an aromatic, heteroaromatic, aliphatic or lipophilic group.

In certain embodiments, the compound may be functionalised with a lipophilic group such as a fatty acyl group. Fatty acyl groups include but are not limited to palmitoyl, butyryl, cerotoyl, decanoyl, docosenoyl, dodecanoyl, eleostearoyl, heptanoyl, hexanoyl, icosanoyl, icosenoyl, lignoceroyl, linoleoyl, lipoyl, myristoleoyl, nonanoyl, octadecanoyl, octanoyl, palmitoleoyl, stearoyl, undecanoyl, and valeryl. Suitably therefore the $R^1$ group may be palmitoyl ([Palm]), i.e.:

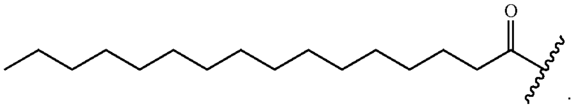 [SMILES: *C(=O)CCCCCCCCCCCCCCC]

.

In one embodiment, the compound may be functionalised with an acyl group. An "acyl" group is a group of the formula $R^{3a}$—C(O)— group wherein $R^{3a}$ is a $C_{1-6}$alkyl, for example formyl, acetyl (Ac), propanoyl, butanoyl, or wherein $R^{3a}$ is benzoyl. Suitably, the $R^{3a}$ group may be $R^{1b}$—C(O)—, such as acetyl (Ac), i.e.:

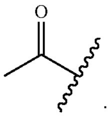 [SMILES: *C(C)=O]

.

In certain embodiments, the $R^1$ group may be substituted with a sugar moiety.

In certain embodiments, one or more amino acid residues in peptides Y and Z may be naturally modified with a sugar moiety, i.e. the amino acid residue may be a "sugar modified analogue". For example, a sugar may be part of a Ser or Thr side chain modification (glycosylation) or a Lys or Arg side chain modification (glycation).

The sugar moieties discussed herein may be a monosaccharide or disaccharide. Examples of monosaccharides include glucose, 6-deoxyglucose, mannose, galactose, glucosamine, galactosamine, N-acetylglucosamine, N-acetylgalactosamine, glucuronic acid, allose, altrose, gulose, idose, fucose, talose, ribose, deoxyribose, arabinose, xylose, lyxose, ribulose, xylulose, fructose, psicose, sorbose or tagatose. Examples of disaccharides include sucrose, lactose, lactulose, allolactose, maltose, isomaltose, isomaltulose, trehalose, cellobiose, kojibiose, nigerose, sophorose, laminaribiose, gentiobiose, thiomaltose, mannobiose or their N-, C- or S-interglycosidic derivative. Most suitably, the sugar moiety is selected from glucosamine or galactosamine. The sugar can be present as an N-terminus modification or as part of Ser sidechain modification. In certain embodiments, the $R^1$ group may be substituted with a phosphate or a sulphate.

In certain embodiments, one or more amino acid residues in peptides Y and Z may be naturally modified with a phosphate or sulphate. For example the phosphate or sulphate may be part of a side chain modification i.e. the amino acid may be phosphorylated or sulphated.

$R^1$ is selected from hydrogen (which may not be noted in the specific peptide sequence, or may instead be designated "H-" or "Hy-"), $C_{1-4}$ alkyl (e.g. methyl, ethyl, propyl, butyl), $—N(R^{1a})—C(=N^+(R^{1b})(R^{1c})NR^{1d}R^{1e}$, or $—C(=N^+(R^{1b})(R^{1c})NR^{1d}R^{1e}$; wherein each of $R^{1a}$, $R^{1b}$, $R^{1c}$, $R^{1d}$ and $R^{1e}$ is independently selected from hydrogen or $C_{1-4}$ alkyl (e.g. methyl, ethyl, propyl, butyl), preferably hydrogen or methyl.

In some embodiments, if $R^1$ is $—C(=N^+(R^{1b})(R^{1c})NR^{1d}R^{1e}$; each of $R^{1a}$, $R^{1b}$, $R^{1c}$, $R^{1d}$ and $R^{1e}$ are methyl, i.e. $R^1$ is $—C(=N^+Me_2)NMe_2$.

When $R^1$="H" (or "Hy";), it typically indicates a free primary amino group at the N-terminus. The other hydrogen atom of the N-terminal amino group is typically invariant, regardless of the nature of $R^1$. Exceptionally, when the residue at the N-terminus is N-methylated, $R^1$ may still be indicated as H even though the N-terminal residue has a secondary amine group. Thus an N-methylated leucine residue at the N-terminus may be indicated as $R^1$-[n-me-L]- where $R^1$ is H. However, it could also be shown as simply $R^1$-L- where $R^1$ is methyl and the other hydrogen atom is not shown.

In some embodiments, an N-terminal glutamine (Gln or Q) or N-terminal glutamic acid (Glu or E) residue may undergo a conversion to form the pyroglutamate terminal group, [pyr]:

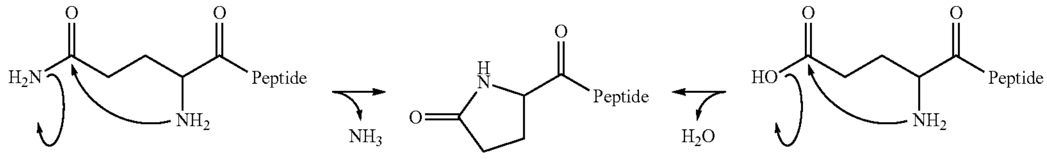

N-terminal Gln N-terminal pyroGlu ([pyr]) N-terminal Glu

An N-terminal glutamine (Q) or glutamic acid (E) residue may undergo such a conversion in biological systems via reaction with certain enzymes. The conversion may also be achieved synthetically.

The $Y^1$ peptide, if present, or the Z peptide may therefore also include an N-terminal [pyr] group:

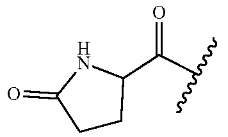 [SMILES: *C(=O)C1CCC(=O)N1]

An N-terminal [pyr] group may be formed as a result of cyclisation of an N-terminal glutamine (Gln or Q) or N-terminal glutamic acid (Glu or E) residue to form the pyroglutamate terminal group. Since this conversion may occur under certain biological conditions, it is considered to be a naturally occurring modification of an N-terminal glutamine (Gln or Q) or N-terminal glutamic acid (Glu or E) residue.

Suitably, $R^2$ is $NH_2$, $NR^{2a}H$, $NR^{2a}R^{2b}$, or $OR^{2a}$; wherein each of $R^{2a}$ and $R^{2b}$ are as defined herein. Preferably $R^2$ is $NH_2$.

A particular example of a kinin peptide according to the invention includes:

| | |
|---|---|
| SB-P-70 | [Hy]-KVKFSAWG-[$NH_2$] (SEQ ID NO: 2) |

or a salt or solvate thereof.

In some embodiments, the compounds of the invention may be in the form of a salt or solvate (e.g. a hydrate).

The compounds of the invention may be provided in combination with one or more additional active insecticides, such as those described herein.

$Y^1$ and $Y^2$

The peptide may comprise one or two further peptide groups located between the terminal R1 and R2 groups at the N and C terminus respectively. Suitably these groups are the $Y^1$ and $Y^2$ group. If present, these groups are located on either side of the Z peptide group.

In one embodiment, the $Y^1$ and $Y^2$ groups are absent.

In one embodiment, the compound comprises a $Y^1$ group only. In one embodiment, the compound comprises a $Y^2$ group only.

In one embodiment, the compound comprises a $Y^1$ and $Y^2$ group.

Suitably the Y groups when present comprise one or two amino acids. Suitably the Y groups may comprise any amino acid, suitably selected from: M, R, G, and K.

In one embodiment, the Y groups are selected from: GR, RG, KR, RK, K, R, M, and G. In one embodiment, the Y groups are selected from: RG, KR, and K.

In one embodiment, the compound comprises a $Y^2$ group only, wherein the $Y^2$ group is selected from RG, KR, and K.

Modified Amino Acid or Non-Natural Amino Acid Analogue

In preferred embodiments, the insecticidal compound does not comprise any modified amino acid or non-natural amino acid analogues.

In particular, preferably peptide $Y^1$, if present does not comprise any a modified amino acid or non-natural amino acid analogues, and peptide $Y^2$ if present does not comprise any modified amino acid or non-natural amino acid analogues. Thus, in certain embodiments, the peptides $Y^1$ and $Y^2$ comprise only unmodified amino acid residues, suitably only natural amino acid residues.

In particular, peptide Z does not comprise any modified amino acid or non-natural amino acid analogues. Thus, in certain embodiments, the peptide Z comprises only unmodified amino acid residues, suitably only natural amino acid residues.

Activity

Suitably, the compounds of the invention have activity against insects. Suitably the activity is against hemipteran insects, dipteran insects, lepidopteran insects and/or blattodean insects.

In a preferred embodiment, the compounds of the invention have activity against lepidopteran insects. The compounds of the invention may therefore find particular use against lepidopteran insects, and find particular application in the associated uses and methods described herein. Particularly preferred lepidopteran insects are moths.

The compounds of the invention typically increase insect mortality, for example when contacted topically to a suitable insect, or ingested by a suitable insect. Thus, the compounds of the invention described herein (and compositions containing them) may be regarded as insecticides, and may be referred to as "insect control agents".

Suitably the compounds of the invention thereby indirectly increase plant health, including increasing plant growth, yields, and the like, due to preventing insect infestations of plants and reducing insect load on plants. Thus, the compounds of the invention described herein (and compositions containing them) may also be regarded as "plant protection agents".

Without wishing to be bound by theory, any or all of the effects described may be mediated by agonist activity at the kinin receptor of the target insects. The kinin receptors believed to be present in target insects include the GPCR kinin receptor. Suitably the compounds of the invention bind to one or more kinin receptors of target insects. Suitably the compounds of the invention have agonist activity when bound to a kinin receptor of a target insect. Suitably the compounds of the invention bind to the kinin receptor. Suitably the compounds of the invention are agonists of the kinin receptor.

Insect Control Agent

The term "insect control agent" refers to agents used to increase insect mortality (i.e. as insecticides). Any compound or composition thereof of the invention may be considered as an insect control agent, and may be used as an insect control agent. Suitably therefore the invention provides the use of a compound or composition of the invention as an insect control agent, for example against diptera insects, hemiptera insects, blattodea insects, and/or lepidoptera insects. Thus an insect control agent may be administered to increase mortality of a given insect or insect population.

An increase in mortality used herein is intended to refer to an increase in the percentage of dead insects, as compared to the percentage of dead insects of an otherwise identical insect population which have not been exposed to the insect control agent of the invention.

Suitably, insect mortality may be calculated as number of dead insects/total number of insects per treated area. Suitably the treated area may be a well of a plate, or may be one or more leaves, or an entire plant. Suitably insect mortality may be measured by performing a leaf dip assay or artificial diet assay as described herein in the examples.

An insect control agent may be used to reduce the size of an insect population, or inhibit growth of an insect population or inhibit feeding of an insect population (e.g. as compared to an otherwise identical insect population not exposed to the agent).

An insect control composition is a composition comprising an insect control agent i.e. a compound of the invention as described.

Plant Protection Agent

The term "plant protection agent" refers to agents used to protect a plant or plant part against insects, e.g. against infestation or colonisation, or being used as a food source by such insects (e.g. by the draining of sap). Any compound or composition thereof of the invention may be considered as a plant protection agent, and may be used as a plant protection agent. Suitably therefore the invention provides the use of a compound or composition of the invention as a plant protection agent, for example to protect a plant against diptera insects, hemiptera insects, blattodea insects, and/or lepidoptera insects.

Infestation or colonisation may be by larvae (or nymphs), by adult insects, or may be by being used as a host or repository for eggs. The terms "infestation" and "colonisation" should not be construed as requiring the presence of the insects to be deleterious to the plant, however.

A plant protection agent may be applied inter alia for reducing insect load on a plant or plant part, for inhibiting or reducing infestation of a plant by insects, for inhibiting (e.g. reducing the rate of) an increase in insect load on a plant or plant part, or for maintaining a plant in an insect-free state, as compared to an otherwise identical plant having an insect population not exposed to the agent. Thus, the plant protection agent may be applied to a plant or plant part which already carries hemipteran, dipteran, blattodean and/or lepidopteran insects, or to a plant or plant part which is free or substantially free of hemipteran, dipteran, blattodean and/or lepidopteran insects.

A plant protection composition is a composition comprising a plant protection agent i.e. a compound of the invention as described.

Plants

By 'plant or plant part', or 'plant or part thereof' referred to herein it is meant any part of a plant including but not limited to; the leaf, stem, root, flower, bud, bulb, and seed.

Suitable plants or parts thereof which may be protected by the compounds or compositions thereof of the invention, or by the agents of the present invention include crops and plants of agricultural, horticultural, or economic significance. Suitable plants may include any of the following or parts thereof: *Musa textilis, Medicago sativa, Prunus dulcis, Pimpinella anisum, Malus sylvestris, Prunus armeniaca, Areca catechu, Arracacia xanthorhiza, Maranta arundinacea, Cynara scolymus, Helianthus tuberosus, Asparagus officinalis, Persea americona, Pennisetum americanum, Vigna subterranean, Musa paradisiaca, Hordeum vulgare, Phaseolus vulgaris, Phaseolus vigna* spp., *Beta vulgaris, Citrus bergamia, Rubus* spp., *Piper nigrum, Acacia meamsii, Vaccinium* spp., *Bertholletia excelsa, Artocarpus altilis, Vicia faba, Brassica oleracea botrytis, Sorghum bicolor, Brassica oleracea gemmifera, Fagopyrum esculentum, Brassica oleracea capitate, Brassica rapa, Brassica* spp., *Theobroma cacao, Cucumis melo, Carum carvi, Elettaria cardamomum, Cynara cardunculus, Ceratonia siliqua, Daucus carota, Anacardium occidentale, Manihot escu-*

*lenta, Ricinus communis, Brassica oleracea botrytis, Apium graveolens, Sechium edule, Prunus* spp., *Castanea sativa, Cicer arietinum, Cichorium intybus, Cichorium intybus, Capsicum* spp., *Cinnamomum verum, Cymbopogon nardus, Citrus medica, Citrus veticulata, Trifolium* spp., *Syzygium aromaticum, Cocos nucifera, Colocasia* spp.; *Xanthosoma* spp., *Coffee* spp., *Cola* spp., *Brassica napus, Zea mays, Valerianella locusta, Gossypium* spp., *Vigna unguiculate, Vaccinium* spp., *Lepidium sativum, Cucumis sativus, Ribes* spp., *Annona reticulata, Colocasia esculenta, Phoenix dactylifera, Moringa oleifera, Phaseolus* spp., *Allium sativum, Allium cepa, Pisum sativum, Triticum durum, Xanthosoma* spp.; *Colocasia* spp., *Solanum melongena, Cichorium endivia, Lygeum spartum, Foeniculum vulgare, Trigonella foenumgraecum, Ficus carica, Cotylus avellane, Furcraea macrophylla, Linum usitatissimum, Phormium tenax, Pelargonium* spp.; *Geranium* spp., *Zingiber officinalis, Langenaria* spp; *Cucurbita* spp., *Cicer arietinum, Citrus paradise, Vitis vinifera, Lygeum spartum, Dactylis glomerata, Arachis hypogaea, Psidium guajava, Cotylus avellane, Cannabis sativa, Crotalaria juncea, Agave fourcroydes, Lawsonia inermis, Humulus lupulus, Armoracia Rusticana, lndigofera tinctorial, Jasminum* spp., *Corchorus* spp., *Brassica oleracea acephala, Ceiba pentandra, Hibiscus cannabinus, Brassica oleracea gongylodes, Lavandula* spp., *Allium ampeloprasum, Citrus limon, Cymbopogon citratus, Lens culinaris, Lespendeza* spp., *Lactuca sativa, Glycyrrhiza glabra, Citrus aurantifolia, Citrus limetta, Linum usitatissimum, Litchi chinensis, Eriobotrya japonica, Lupinus* spp., *Macadamia* spp., *Myristica fragrans, Agave atrovirens, Citrus reticulata, Mangifera indica, Manihot esculenta, Secale cereal, Mespilus germanica, Cucumis melo, Penicum miliaceum, Eleusine coracana, Setaria italica, Echinochloa crusgalli, Eleusine coracana; Mentha* spp., *Morus* spp., *Morus alba, Agaricus* spp.; *Pleurotus* spp. *Volvariella, Brassica nigra; Sinapis alba, Prunus persica, Phormium tenax, Guizotia abyssinica, Myristica fragrans, Avena* spp., *Elaeis guineensis, Abelmoschus esculentus, Olea europea, Papaver somniferum, Citrus sinensis, Citrus aurantium, Dactylis glomerate, Metroxylon* spp., *Borassus flabellifer, Carica papaya, Pastinaca sativa, Pyrus communis, Pisum sativum, Carya illinoensis, Capsicum annuum, Diospyros kaki; Diospyros virginiana, Cajanus cajan, Ananas comosus, Pistacia* spp., *Prunus domestica, Punica granatum, Citrus grandis, Solamum tuberosum, Ipomoea batatas, Cucurbita* spp., *Chrysanthemum cineraraiefolium, Aspidosperma* spp., *Cydonia oblonga, Cinchona* spp., *Chenopodium quinoa, Raphanus sativus* (including *Cochlearia armoracia*), *Boehmeria nivea, Agrostis* spp., *Boehmeria nivea, Rheum* spp., *Oryza sativa; Oryza glaberrima, Rose* spp., *Hevea brasiliensis, Secale cereal, Lolium* spp., *Carthamus tinctorius, Metroxylon* spp., *Onobrychis viciifolia, Valerianella locusta, Tragopogon porrifolius, Achras sapota, Citrus reticulata, Brassica ileracea capitate, Scorzonera hispanica, Sesamum indicum, Butyrospermum paradoxum, Agave sislana, Citrus aurantifolia, Glycine max, Triticum spelta, Spinacia oleracea, Secale cereal, Cucurbita* spp., *Fragaria* spp., *Sorghum bicolor Sudanense, Saccharum officinarum, Helianthus annuus, Crotalaria juncea, Citrus limetta, lopmoea batatas, Citrus reticulata, Xanthosoma sagittifolium, Manihot esculenta, Colocasia esculenta, Camellia sinensis, Eragrostis abyssinica, Phleum pratense, Nicotiana tabacum, Lycopersicum esculentum, Lotus* spp., *Aleurites* spp., *Brassica rapa, Urena lobate, Vanilla planifolia, Vicia sativa, Juglans* spp., *Citrullus lanatus, Acacia meamsii, Triticum* spp., *Hordeum* spp., *Dioscorea* spp., and *Ilex paraguariensis.*

Suitably, the plant or part thereof which may be protected by the compounds, compositions, or agents of the present invention is selected from a plant or part thereof which suffers from hemipteran, dipteran, blattodean and/or lepidopteran insect infestations, or which attracts hemipteran, dipteran, blattodean and/or lepidopteran insects. Suitably, the plant or part thereof which suffers from hemipteran, dipteran, blattodean and/or lepidopteran insect infestations, or which attracts hemipteran, dipteran, blattodean and/or lepidopteran insects is any of those listed above.

Suitably, the plant or part thereof which suffers from hemipteran insect infestations, or which attracts hemipteran insects, is any of those listed above.

Suitably, the plant or part thereof which suffers from dipteran insect infestations, or which attracts dipteran insects, is any of those listed above.

Suitably, the plant or part thereof which suffers from lepidopteran insect infestations, or which attracts lepidopteran insects, is any of those listed above.

Suitably, the plant or part thereof which suffers from blattodean insect infestations, or which attracts blattodean insects, is any of those listed above.

In one embodiment, the plant or part thereof is selected from a plant or part thereof which suffers from or attracts hemipteran insect infestations, for example: cereal crops such as wheat (*Triticum* spp.), oats (*Avena* spp), rye (*Secale* spp.), barley (*Hordeum* spp.), rice (*Oryza* spp.) and corn (*Zea* spp.); fruit and vegetable crops including apples (*Malus* spp); pears (*Pyrus* spp); strawberry (*Fragaria* spp.), blueberry (*Vaccinum* spp.), blackberry (*Rubus* spp.), raspberry (*Rubus* spp.), citrus (*Citrus* spp.), olive (*Olea* spp.), durian (*Durio* spp.), longan (*Dimocarpus* spp.), litchi (*L. chinensis*), persimmon (*Diospyros* spp.); beans and peas (including but not limited to *Phaseolus, Vigna, Pisum, Lens, Glycine, Cicer, Cajanus, Arachis* spp), sugar beet (*Beta vulgaris*), sugar cane (*Saccharum* spp.), lettuce (*Lactuca* spp.), brassicas (*Brassica* spp.) including oil seed rape, alliums (*Allium* spp.), tomato (*Solanum* spp.), pepper (*Capsicum* spp.), asparagus (*A. officinalis*), melon, squash, pumpkins (*Cucumis* spp.), and tubers (potato) (*Solanum* spp.), or a part thereof.

In one embodiment, the plant or part thereof is selected from a plant or part thereof which suffers from or attracts aphid insect infestations, suitably *M. persicae* insect infestations, including *Solanaceae, Cruciferae*, and *Leguminosae* for example: cereal crops such as wheat (*Triticum* spp including winter wheat *Triticum aestivum* L); fruit and vegetable crops including peach (*Prunus* spp.), strawberry (*Fragaria* spp.), blueberry (*Vaccinum* spp.), blackberry (*Rubus* spp.), raspberry (*Rubus* spp.), brassicas (*Brassica* spp.) such as oil seed rape, lettuce (*Lactuca* spp.), tomato (*Solanum* spp.), pepper (*Capsicum* spp.), beans and peas (including but not limited to *Vigna, Pisum* spp), melon, squash, pumpkins (*Cucumis* spp.), citrus (*Citrus* spp.), and tubers (potato) (*Solanum* spp.), or a part thereof. In one embodiment, the plant is a vegetable crop, suitably a *Brassica* spp.

In one embodiment, the plant or part thereof is selected from a plant or part thereof which suffers from or attracts dipteran insect infestations, for example: cereals (*Triticum* spp.); oats (*Avena* spp); rye (*Secale* spp.); barley (*Hordeum* spp,) rice (*Oryza* spp.) and corn (*Zea* spp.); beans and peas (including but not limited to *Phaseolus, Vigna, Pisum, Lens, Glycine, Cicer, Cajanus, Arachis* spp); fruit crops including apples (*Malus* spp), pears (*Pyrus* spp), strawberry (*Fragaria* spp.), blueberry (*Vaccinum* spp.), blackberry (*Rubus* spp.), raspberry (*Rubus* spp.), cherry, plum, apricot, peach, nectarine (*Prunus* spp.), blackcurrant, redcurrant, whitecurrant, gooseberry (*Ribes* spp.), kiwi fruit (*Actinidia* spp), papaya (*Carica* spp.), avocado (*Persea* spp.), mango (*Mangifera indica* L), longan (*Dimocarpus* spp.), litchi (*L. chinensis*), grapes (*Vitis* spp.), fig (*Ficus* spp.), passionfruit (*Passiflora* spp.), Asian pears (*Pyrus* spp), citrus (*Citrus* spp.), and olive (*Olea* spp.); vegetable crops including alliums (*Allium* spp.), aubergine, tomato (*Solanum* spp.) and peppers (*Capsicum* spp.), lettuce (*Lactuca* spp.), brassicas (*Brassica* spp.) and courgette, melon, squash, pumpkins (*Cucumis* spp.); Apiaceae root crops including carrot (*Daucus* spp.), parsnip (*Pastinaca* spp.), or a part thereof.

In one embodiment, the plant or part thereof is selected from a plant of part thereof which suffers from or attracts lepidoptera insect infestations, for example: cereal crops such as wheat (*Triticum* spp.), oats (*Avena* spp), rye (*Secale* spp.), barley (*Hordeum* spp.), rice (*Oryza* spp.) and corn (*Zea* spp.); fruit and vegetable crops including apples (*Malus* spp); pears (*Pyrus* spp); tree nuts (including for example almonds (*P. amygdalus*), pistachio (*Pistacia vera*), walnuts (*Juglandaceae*), hazlenuts (*Cotylus*)); avocado, including Persea Americana (*Lauraceaea*), blueberry (*Vaccinum* spp.), citrus (*Citrus* spp.), olive (*Olea* spp.), durian (*Durio* spp.), longan (*Dimocarpus* spp.), litchi (*L. chinensis*), persimmon (*Diospyros* spp.); beans and peas (including but not limited to *Phaseolus, Vigna, Pisum, Lens, Glycine, Cicer, Cajanus, Arachis* spp), sugar beet (*Beta vulgaris*), sugar cane (*Saccharum* spp.), lettuce (*Lactuca* spp.), brassicas (*Brassica* spp.) including oil seed rape, alliums (*Allium* spp.), tomato (*Solanum* spp.), pepper (*Capsicum* spp.), asparagus (*A. officinalis*), melon, squash, pumpkins (*Cucumis* spp.), and tubers (potato) (*Solanum* spp.), or a part thereof.

Insects

The compounds, compositions, and agents of the invention suitably have activity against insects as described above.

The compounds, compositions, and agents of the invention may be effective against any insects. Such as Arthropoda, in particular from the class of the arachnids, for example *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia praetiosa, Centruroides* spp., *Chorioptes* spp., *Dermanyssus gallinae, Dermatophagoides pteronyssius, Dermatophagoides farinae, Dermacentor* spp., *Eotetranychus* spp., *Epitrimerus pyri, Eutetranychus* spp., *Eriophyes* spp., *Halotydeus destructor, Hemitarsonemus* spp., *Hyalomma* spp., *Ixodes* spp., *Latrodectus* spp., *Loxosceles* spp., *Metatetranychus* spp., *Nuphersa* spp., *Oligonychus* spp., *Ornithodorus* spp., *Ornithonyssus* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vaejovis* spp., *Vasates lycopersici.*

Still other examples are from the order of the Anoplura (Phthiraptera), for example, *Damalinia* spp., *Haematopinus* spp., *Linognathus* spp., *Pediculus* spp., *Ptirus pubis, Trichodectes* spp.

Still other examples are from the order of the Chilopoda, for example, *Geophilus* spp., *Scutigera* spp.

Still other examples are from the order of the Collembola, for example, *Onychiurus armatus.*

Still other examples are from the order of the Diplopoda, for example, *Blaniulus guttulatus.*

Still other examples are from the order of the Diptera, for example, *Aedes* spp., *Agromyza* spp., *Anastrepha* spp., *Anopheles* spp., *Asphondylia* spp., *Bactrocera* spp., *Bibio hortulanus, Calliphora erythrocephala, Ceratitis capitata, Chironomus* spp., *Chrysomyia* spp., *Chrysops* spp., *Cochliomyia* spp., *Contarinia* spp., *Cordylobia anthropophaga, Culex* spp., *Culicoides* spp., *Culiseta* spp., *Cuterebra* spp., *Dacus oleae, Dasyneura* spp., *Delia* spp., *Dermatobia hominis, Drosophila* spp., *Echinocnemus* spp., *Fannia* spp., *Gasterophilus* spp., *Glossina* spp., *Haematopota* spp., *Hydrellia* spp., *Hylemyia* spp., *Hyppobosca* spp., *Hypoderma* spp., *Liriomyza* spp., *Lucilia* spp., *Lutzomia* spp., *Mansonia* spp., *Musca* spp., *Nezara* spp., *Oestrus* spp., *Oscinella fit, Pegomyia* spp., *Phlebotomus* spp., *Phorbia* spp., *Phormia* spp., *Prodiplosis* spp., *Psila rosae, Rhagoletis* spp., *Sarcophaga* spp., *Simulium* spp., *Stomoxys* spp., *Tabanus* spp., *Tannia* spp., *Tetanops* spp., *Tipula* spp. Still other examples are from the order of the Heteroptera, for example, *Anasa tristis, Antestiopsis* spp., *Boisea* spp., *Blissus* spp., *Calocoris* spp., *Campylomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp. Still other examples are from the order of the Homoptera, for example, *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma pin, Aphis* spp., *Arboridia apicalis, Aspidiella* spp., *Aspidiotus* spp., *Atanus* spp., *Aulacorthum solani, Bemisia* spp., *Brachycaudus helichtysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis etysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

Still other examples are from the order of the Hymenoptera, for example, *Acromyrmex* spp., *Athalia* spp., *Atta* spp.,

*Diprion* spp., *Hoplocampa* spp., *Lasius* spp., *Monomorium pharaonis, Solenopsis invicta, Tapinoma* spp., *Vespa* spp.

Still other examples are from the order of the Isopoda, for example, *Armadillidium vulgare, Oniscus asellus, Porcellio scaber.*

Still other examples are from the order of the Isoptera, for example, *Coptotermes* spp., *Cornitermes cumulans, Ctyptotermes* spp., *lncisitermes* spp., *Microtermes obesi, Odontotermes* spp., *Reticulitermes* spp.

Still other examples are from the order of the Lepidoptera, for example, *Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Chematobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia* spp., *Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamestra brassicae, Mods* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plodia interpunctella, Plusia* spp., *Plutella xylostella, Prays* spp., *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix* spp., *Trichophaga tapetzella, Trichoplusia* spp., *Tuta absoluta, Virachola* spp.

Still other examples are from the order of the Orthoptera, for example, *Acheta domesticus, Dichroplus* spp., *Gryllotalpa* spp., *Leucophaea maderae, Locusta* spp., *Melanoplus* spp., *Pulex irritans, Schistocerca gregaria.*

Still other examples are from the order of the Blattodea, for example, *Blatta orientalis, Blattella germanica, Periplaneta america, Periplaneta* spp., *Supella longipalpa*, termites of the infraorder Isoptera such as those of the family Termitidae.

Still other examples are from the order of the Siphonaptera, for example, *Ceratophyllus* spp., *Ctenocephalides* spp., *Tunga penetrans, Xenopsylla cheopis.*

Still other examples are from the order of the Symphyla, for example, *Scutigerella* spp.

Still other examples are from the order of the Thysanoptera, for example, *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp. Still other examples are from the order of the Zygentoma (=Thysanura), for example, *Lepisma saccharina, Thermobia domestica.* for example *Lepisma saccharina, Thermobia domestica.*

In one preferred embodiment, the compounds, compositions, and agents of the invention suitably have activity against insects of the order hemiptera, diptera, blattodea and/or lepidoptera. In one preferred embodiment, the compounds, compositions, and agents of the invention suitably have activity against insects of the order Lepidoptera. In one preferred embodiment, the compounds, compositions, and agents of the invention suitably have activity against moths. In one embodiment, the compounds, compositions, and agents of the invention suitably have activity against the moth species *Plutella xylostella*. In one embodiment, the compounds, compositions, and agents of the invention suitably have activity against the moth species *Spodoptera frugiperda*.

Hemipteran Insects

The compounds, compositions and agents of the invention suitably have activity against insects of the order Hemiptera, which comprises groups including aphids, planthoppers, leafhoppers, stink bugs, shield bugs and cicadas. Suitably, the compounds, compositions and agents of the invention suitably have activity against aphids.

Hemipterans are defined by distinctive mouthparts in the form of a “beak”, comprising modified mandibles and maxillae which form a “stylet”, sheathed within a modified labium.

Many insects within these groups have endogenous neuropeptides with sequence homology to the peptides described herein, suggesting that the compounds of the present invention may have activity against those insects.

The insects may belong to the sub-order Sternorrhyncha, e.g. to the superfamily of Aphidoidea (aphid superfamily), Aleyrodoidea (whiteflies), Coccoidea (scale insects), Phylloxeroidea (including Phylloxeridae or “phylloxerans”, and Adelgidae or woolly conifer aphids) or Psylloidea (jumping plant lice etc.).

Thus, the insects may be aphids, i.e. members of the aphid superfamily (Aphidoidea). Aphids (Hemiptera: Aphididae) are one of the most significant groups of agricultural pests and are vectors in the transmission of approximately 50% of all insect transmitted plant viruses. Within that superfamily, the aphids may be part of the family Aphididae, which contains sub-families Aiceoninae, Anoeciinae, Aphidinae, Baltichaitophorinae, Calaphidinae, Chaitophorinae, Drepanosiphinae, Eriosomatinae, Greenideinae, Hormaphidinae, Israelaphidinae, Lachninae, Lizeriinae, Macropodaphidinae, Mindarinae, Neophyllaphidinae, Phloeomyzinae, Phyllaphidinae, Pterastheniinae, Saltusaphidinae, Spicaphidinae, Taiwanaphidinae, Tamaliinae and Thelaxinae.

The aphids may, for example, be of the genus *Acyrthosiphon* (e.g. *Acyrthosiphon pisum*), *Aphis* (e.g. *Aphis gossypii, Aphis glycines, Aphis fabae*), *Diuraphis* (e.g. *Diuraphis noxia*) *Macrosiphum* (e.g. *Macrosiphum rosae, Macrosiphum euphorbiae*), *Myzus* (e.g. *Myzus persicae*), *Rhopalosiphum* (e.g. *Rhopalosiphum padi*), or *Sitobion* (e.g. *Sitobion avenae*).

*Myzus persicae* (peach potato aphid) is the most economically important aphid crop pest worldwide, with a global distribution and host range encompassing more than 400 species in 40 different plant families. For example, it is a major pest of agricultural crops including fruit and potatoes, and act as a vector for viruses.

*Macrosiphum rosae*, (rose aphid) is an important horticultural pest, especially of cultivated species of *Rosa*, and is a vector in the transmission of 12 plant viruses including the strawberry mild yellow edge virus.

*Aphis gossypii* (cotton or melon aphid) is a pest of Curcibitae and cotton.

Other than aphids, the insects may, for example, be of the Adelgidae family, e.g. of the genus *Adelges* (e.g. *Adelges tsugae*).

The insects may be of the Aleyrodidae family, e.g. of the genus *Bemisia* (e.g. *Bemisia tabac*;) or *Trialeurodes* (e.g. *Trialeurodes vaporariorum*).

The insects may be of the Psylloidea family, e.g. of the genus *Pachypsylla* (e.g. *Pachypsylla venusta*).

As examples of hemipteran insects outside the sub-order Sternorryncha, the insects may be of the Cimicidae family, e.g. of the genus *Cimex* (bed bugs), e.g. *Cimex lectularius.*

The insects may be of the Cicadellidae family, e.g. of the genus *Cuerna* (e.g. *Cuerna arida*), *Graminella* (e.g. *Graminella nigrifrons*) or *Homalodisca* (e.g. *Homalodisca vitripennis*). Also included in the Cicadellidae family are *Amrasca biguttula.*

The insects may be part of the Delphacidae family, e.g. of the genus *Nilaparvata* (e.g. *Nilaparvata lugens*) or *Sogatella* (e.g. *Sogatella furcifera*). For example, *Nilaparvata lugens* (brown planthopper) is a pest of rice crops, especially in Asia.

The insects may be of the Liviidae family, e.g. of the genus *Diaphorina* (e.g. *Diaphorina citri*).

The insects may be part of the Miridae family, e.g. of the genus *Pseudatomoscelis* (e.g. *Pseudatomoscelis seriatus*), Lygus (e.g. *Lygus hesperus*) or *Tupiocoris* (e.g. *Tupiocoris notatus*). For example, *Pseudatomoscelis seriatus* (cotton fleahopper) is a pest of cotton.

The insects may be of the Pentatomidae family, e.g. of the genus *Acrosternum* (e.g. *Acrosternum hilare*), *Banasa* (e.g. *Banasa dimiata*), *Euschistus* (e.g. *Euschistus servus, Euschistus heroes*), *Halyomorpha* (e.g. *Halyomorpha halys*), *Murgantia* (e.g. *Murgantia histrionica*), *Nezara* (e.g. *Nezara viridula*), *Plautia* (e.g. *Plautia stali*), or *Podisus* (e.g. *Podisus maculiventris*). For example, *Acrosternum hilare* (green stink bug) is a significant pest of cotton. *Euschistus servus* (brown stink bug) is a pest of many agricultural crops including seeds, grains, nuts and fruits, especially in the southern USA. *Nezara viridula* is a pest of grain and soybean crops, especially in Brazil.

The insects may be of the Pyrrhocoridae family, e.g. of the genus *Pyrrhocoris* (e.g. *Pyrrhocoris apterus*).

The insects may be of the Reduviidae family, e.g. of the genus *Rhodnius* (e.g. *Rhodnius prolixus*), or *Triatoma* (e.g. *Triatoma infestans*). *Rhodnius prolixus* is a vector of human disease (Chagas disease).

The insects may be of the Triozidae family, e.g. of the genus *Acanthocasuarina* (e.g. *Acanthocasuarina muellerianae*).

In one embodiment, the insect may be selected from the following species: *H. halys, E. heroes, A. hilare, A. gossypii, E. servus, M. persicae, N. viridula, N. lugens, P. seriatus,* and *R. prolixus.*

In one embodiment, the insect is of the species *M. persicae.*

Dipteran Insects

The compounds, compositions and agents of the invention may have activity against insects of the order Diptera.

In particular, they may have activity against insects of the family Drosophilidae, such as fruit flies, including those of genus *Drosophila*, such as *Drosophila suzukii*. They may also have activity against insects of the family Tephritidae, including those of the genera *Anastrepha* (*Anastrepha* spp.); *Bactrocera* (*Bactrocera* spp.); *Ceratitis* (*Ceratitis* spp.); *Dacus* (*Dacus* spp.); *Rhagoletis* (*Rhagoletis* spp.); *Tephritis* (*Tephritis* spp.).

The families Drosophilidae and Tephritidae together are commonly referred to as fruit flies.

The compounds, compositions, and agents may also have activity against other important dipteran pests, such as flies of the family Chloropidae (chloropid flies) and those of the genera:

*Phytomyza* (e.g. *Phytomyza angelicastri*);
*Melani* (e.g. *Melani agromyza*);
*Antherigona* (e.g. *Antherigona* spp);
*Delia* (e.g. *Delia radicum*);
*Contarinia* (e.g. *Contarinia sorghicola*);

For more detail on these, and other examples, see *Developing the Arsenal Against Pest and Vector Dipterans: Inputs of Transgenic and Paratransgenic Biotechnologies, Ogaugwu and Durvasula, IntechOpen,* 2017: DOI:10.5772/66440

Lepidopteran Insects

The compounds, compositions and agents of the invention may have activity against insects of the order Lepidoptera.

In particular, they may have activity against insects of the genera: *Heliothis, Plutella, Spodoptera*, and *Cydia*. Suitably the compounds, compositions and agents of the invention may have activity against the species: *Heliothis peltigera, H. virescens, Spodoptera* spp., and *Cydia pomonella* (Codling Moth), Larvae of *Heliothis* spp., including *peltigera* and *virescens Spodoptera littoralis* (which represent a large variety of *Heliothinae* and *Spodoptera* moth species and are world-wide agricultural pests), and *Plutella xylostella* (diamondback moth, most important world-wide pest of *Brassicas*).

In one embodiment, the compounds, compositions and agents of the invention may have activity against *Plutella xylostella*. In one embodiment, the compounds, compositions and agents of the invention may have activity against *Spodoptera frugiperda.*

Blattodean Insects

The compounds, compositions and agents of the invention may have activity against insects of the order Blattodea.

In particular, they may have activity against insects of the infraorder Isoptera. Suitably the compounds, compositions and agents of the invention may have activity against the species of the family Termitidae.

Suitably the compounds, compositions and agents of the invention may have activity against the species: *Blatta orientalis, Blattella germanica, Periplaneta america, Periplaneta* spp., *Supella longipalpa.*

Household Pests

The compounds, compositions, and agents of the invention may also have activity against domestic pests, such as cockroaches and termites (such as those of the family Termitidae). Of more than 3000 species, these may include the German cockroach (*Blattella germanica*), the Oriental cockroach (*Blatta orientalis*), the American cockroach (*Periplaneta americana*) and the brown banded cockroach (*Supella longipalpa*). Cockroaches are common domestic pests worldwide, and may carry various diseases. Control of these and other domestic pests (e.g. ants) is envisaged by treating surfaces where the insects run, but particularly with food baits containing compounds, compositions and agents of the invention, and with direct spray application of compounds, compositions and agents of the invention.

Therefore further aspects of the invention may include a bait comprising a compound or composition of the invention, suitably which may be a bait for domestic pests. Further aspects of the invention may include a method of controlling domestic pests, reducing domestic pest populations, inhibiting domestic pest populations, increasing domestic pest mortality, the method comprising treating a surface (e.g. wood) which is contacted by the domestic pest with a compound or composition of the invention, or contacting the domestic pest with a compound or composition of the invention. Further details of such methods are described hereinbelow. Optionally treating or contacting may comprise a suitable means of application as described elsewhere herein, such as by spraying. Suitably therefore a sprayable formulation comprising a compound or composition of the invention is also envisaged. Suitable formulations are described elsewhere herein.

Methods and Uses of the Invention

Methods of Increasing Insect Mortality

The invention provides a method of increasing insect mortality, comprising contacting an insect or insect population with a compound, composition or combinations as described herein. The insect or insect population may be hemipteran, dipteran, blattodean, and/or lepidopteran insects.

In one embodiment, there is provided a method of increasing dipteran insect mortality, comprising contacting a dipteran insect or dipteran insect population with a compound or composition or combinations of the invention.

In one particular embodiment, there is provided a method of increasing *Drosophila suzukii* mortality, comprising contacting a *Drosophila suzukii* insect or insect population with a compound or composition or combinations of the invention.

In one embodiment, there is provided a method of increasing hemipteran insect mortality, comprising contacting a hemipteran insect or hemipteran insect population with a compound or composition or combinations as defined herein.

In one particular embodiment, there is provided a method of increasing aphid mortality, comprising contacting an aphid insect or insect population with a compound or composition or combinations as defined herein.

In one particular embodiment, there is provided a method of increasing *Aphis fabae, Aphis gossypii, Acyrthosiphon pisum, Myzus persicae, Amrasca biguttula* or *Rhopalosiphum padi* mortality, comprising contacting an *Aphis fabae, Aphis gossypii, Acyrthosiphon pisum, Myzus persicae, Amrasca biguttula* or *Rhopalosiphum padi* insect or insect population with a compound or composition or combinations as defined herein.

In one particular embodiment, there is provided a method of increasing *Myzus persicae* mortality, comprising contacting a *Myzus persicae* insect or insect population with a compound or composition or combinations as defined herein.

In one particular embodiment, there is provided a method of increasing *Rhopalosiphum padi* mortality, comprising contacting a *Rhopalosiphum padi* insect or insect population with a compound or composition or combinations as defined herein.

In one embodiment, there is provided a method of increasing lepidoptera insect mortality, comprising contacting a lepidopteran insect or lepidopteran insect population with a compound or composition or combinations as defined herein.

In one particular embodiment, there is provided a method of increasing *Plutella xylostella* mortality, comprising contacting a *Plutella xylostella* insect or insect population with a compound or composition or combinations as defined herein.

In one particular embodiment, there is provided a method of increasing *Spodoptera frugiperda* mortality, comprising contacting a *Spodoptera frugiperda* insect or insect population with a compound or composition or combinations as defined herein.

In one embodiment, there is provided a method of increasing blattodean insect mortality, comprising contacting a blattodean insect or blattodean insect population with a compound or composition or combinations as defined herein.

Methods of Inhibiting or Reducing infestation of a Plant or Site

The invention further provides a method of inhibiting infestation of a plant or plant part by insects, suitably by hemipteran, dipteran, blattodean and/or lepidopteran insects comprising contacting the plant or plant part with a compound, composition or combinations as described.

In one embodiment, there is provided a method of inhibiting infestation of a plant by dipteran insects comprising contacting the plant with a compound or composition or combinations of the invention.

In one particular embodiment, there is provided a method of inhibiting infestation of a plant by *Drosophila suzukii* comprising contacting the plant with a compound or composition or combinations of the invention.

In one embodiment, there is provided a method of inhibiting infestation of a plant by hemipteran insects comprising contacting the plant with a compound or composition or combinations as defined herein.

In one embodiment, there is provided a method of inhibiting infestation of a plant by aphids comprising contacting the plant with a compound or composition or combinations as defined herein.

In one embodiment, there is provided a method of inhibiting infestation of a plant by *Aphis fabae, Aphis gossypii, Acyrthosiphon pisum, Myzus persicae* or *Rhopalosiphum padi* comprising contacting the plant with a compound or composition or combinations as defined herein.

In one particular embodiment, there is provided a method of inhibiting infestation of a plant by *Rhopalosiphum padi* comprising contacting the plant with a compound or composition or combinations as defined herein.

In one embodiment, there is provided a method of inhibiting infestation of a plant by *Myzus persicae* comprising contacting the plant with a compound or composition or combinations as defined herein.

In one embodiment, there is provided a method of inhibiting infestation of a plant by *Halyomorpha halys* comprising contacting the plant with a compound or composition or combinations as defined herein.

In one embodiment, there is provided a method of inhibiting infestation of a plant by lepidopteran insects comprising contacting the plant with a compound or composition or combinations as defined herein.

In one embodiment, there is provided a method of inhibiting infestation of a plant by *Plutella xylostella* comprising contacting the plant with a compound or composition or combinations as defined herein.

In one embodiment, there is provided a method of inhibiting infestation of a plant by *Spodoptera frugiperda* comprising contacting the plant with a compound or composition or combinations as defined herein.

In one embodiment, there is provided a method of inhibiting infestation of a plant by blattodean insects comprising contacting the plant with a compound or composition or combinations as defined herein.

The invention further provides a method of inhibiting infestation of a site on which plants are growing or intended to be grown by insects, suitably by hemipteran, dipteran, blattodean and/or lepidopteran insects comprising contacting the site with a compound, composition, or combinations as described.

The method may be prophylactic. Thus, for example, the compound may be applied to the plant or plant part, or site, while the plant or part or field is free or substantially free of insects.

Suitably the site may be any agricultural site suitable for growing plants. Suitably the site may be any area or locale which may be suitable for growing plants, or in which plants are grown. Suitable sites may include farmland, brownfield sites, fields, greenhouses, conservatories, containers, aquaponics and hydroponics systems etc. In one embodiment, the site is a field.

Alternatively, the plant or plant part or site may already be colonised or infested by insects, suitably by hemipteran, dipteran, blattodean and/or lepidopteran insects.

Thus, the invention further provides a method of reducing insect infestation of a plant or plant part, or of reducing insect load on a plant or plant part, the method comprising contacting the plant or plant part with a compound, composition, or combinations as described herein. The invention also provides a method of reducing insect infestation of a field, or of reducing an insect load in a field, the method comprising contacting the field with a compound, composition, or combinations as described herein. Suitably of hemipteran, dipteran, blattodean and/or lepidopteran insects.

Methods of Decreasing Insect Feeding

The invention further provides a method of decreasing insect feeding, comprising contacting an insect or insect population with a compound, composition or combinations as described herein. Suitably decreasing insect feeding on a plant or plant part. The insect or insect population may be hemipteran, dipteran, blattodean and/or lepidopteran insects.

Methods of Protecting a Plant From Insects

The invention further provides a method of protecting a plant or part thereof from insects, or from insect infestation, and specifically a method of protecting a plant or plant part against hemipteran, dipteran, blattodean and/or lepidopteran insects or infestation thereof, wherein the method comprises the step of applying directly or indirectly to the plant or to a part of the plant, an insecticidal compound or composition, or combinations of the invention. Suitably applying indirectly may comprise applying the compound or composition or combinations of the invention to the field or locale in which the plant is growing, or in which it is intended to be grown.

The present invention also provides post-harvest treatment methods for protecting or treating a harvested plant or a harvested part of the plant against insects, or insect infestation, specifically against hemipteran, dipteran, blattodean and/or lepidopteran insects or infestation thereof, the method comprising the step of applying directly or indirectly to the harvested plant or to a harvested part of the plant, an insecticidal compound or composition or combinations of the invention, under conditions effective to protect or treat the harvested plant or a harvested part of the plant against the insects. Suitably applying indirectly may comprise applying the compound or composition or combinations of the invention to the location in which the plant or a harvested part of the plant is stored, or in which it is intended to be stored.

Suitably the insect may be of the order hemiptera, diptera, blattodea and/or lepidoptera.

Methods of Contacting an Insect

In one embodiment, there is provided a method of contacting an insect with a compound, preferably an insect control agent, even more preferably an insecticide, said method comprising applying to or on sites frequented by the insect a compound or composition or combinations according to the invention.

The site, frequented by insects may be a natural habitat for insects, or a place regularly visited by insects. This site can be treated then with the compound or composition as described above: as a non-limiting example mosquito nets, impregnated with encapsulated insecticide, can be used as application method. Alternatively, said site is created by application of a visual lure or of an attractant for the insects. Visual lures are known to the person skilled in the art, and include but are not limited to light sources, coloured object and shapes or silhouettes that stand out of a contrasting background. As mentioned above, insect attractants include but are not limited to pheromones, kairomones and allomones. The attractant may be present in the composition or it may be applied separately from the compound or composition or combinations, to ensure that the insects are attracted to the site where the compound or composition or combinations is applied.

Suitably the insect may be of the order hemiptera, diptera, blattodea and/or lepidoptera. More suitably, the insect is of the order lepidoptera. Most suitably, the insect is an moth, such as *Plutella xylostella* or *Spodoptera frugiperda.*

Application of the Compounds or Compositions

The compound or composition or combinations of the invention may be contacted with the insect or insect population, suitably this may comprise applying the compound or composition or combinations directly to an insect or insect population. For example, it may be applied topically. Alternatively, the compound or composition or combinations may be applied indirectly. For example, it may be applied to a substrate, site, or locale likely to come into contact with an insect or insect population. The substrate may be a plant or plant part, especially for Hemiptera or Diptera or Blattodea or Lepidoptera which represent pests of plants (whether crops or horticultural plants), or may be a field, locale, or area suitably in which the plants are grown. Suitably therefore the compound or composition or combinations may be applied to the plant or plant part. Suitably therefore the compound or composition or combinations may be applied to the site in which the plant is grown.

However, for insects which represent pests to humans, such as the Cimicidae family (e.g. bedbugs of the genus *Cimex*, such as *Cimex lectularius*) or the Reduviidae family (e.g. of the genus *Rhodnius* such as *Rhodnius prolixus*, or *Triatoma* such as *Triatoma infestans*) which can be vectors of human disease, the substrate may be a domestic surface or article, such as bedding, a mattress, or any other suitable domestic surface. The compound or composition may be applied to the substrate in a form suitable for ingestion by an insect.

Suitably contacting may comprise feeding or spraying, for example. Suitably feeding may be encouraged via bait attractants, which may be comprised in a composition of the invention, as explained below.

The methods may comprise contacting or applying directly or indirectly to the plant or to a part of the plant a compound or composition or combinations as disclosed herein, for example at an application rate higher than 5 g of the compound per hectare, such as but not limited to an application rate higher than 10 g of the compound per hectare, such as an application rate higher than 24 g of the compound per hectare, such as an application rate higher than 50 g of the compound per hectare, such as an application rate higher than 75 g of the compound per hectare, such as an application rate higher than 100 g of the compound per hectare, or in particular an application rate higher than 200 g of the compound per hectare. These methods may comprise applying directly or indirectly to the plant or to a part of the plant a compound, composition or combinations as disclosed herein, for example at an application rate between 5 g and 100 g of the compound composition or combinations per hectare, such as but not limited to an application rate of between 5 g and 200 g of the compound composition or combinations per hectare, in particular an application rate of between 5 g and 50 g of the compound composition or combinations per hectare, such as between 5 g and 30 g of the compound composition or combinations per hectare or between 10 g and 25 g per hectare.

The compounds or compositions or combinations as disclosed herein may be directly or indirectly contacted with/applied to the plant or to a part of the plant by spraying, atomizing, foaming, fogging, culturing in hydroculture, culturing in hydroponics, coating, submerging, injecting and/or encrusting, optionally post-harvest. Suitably contacting may comprise feeding or spraying, for example. In some embodiments, the contacting is by feeding. Contacting may comprise injecting a plant (e.g. a tree) or part thereof with the composition as defined herein, using systems and methods such as those described in WO2020/021041, WO2023/161802, WO2022/264053, WO2022/189386, WO2022/165248, WO2021/152093, WO2020/212612 and WO2020/021041, the entire contents of which being incorporated by reference.

Suitably the compound may be contacted with the insect or insect population, or plant or plant part, at any suitable concentration which is effective. Suitably the compositions and combinations may comprise such an effective concentration of a compound. Suitably the concentration of the compound is between $10^{-3}$ to $10^{-9}$ M, suitably between $10^{-4}$ to $10^{-6}$ M, suitably between $10^{-4}$ to $10^{-5}$ M.

Use as a Plant Protection Agent

The invention further provides the use of a compound, composition or combination as described herein as a plant protection agent, and specifically for protecting a plant or plant part against insects, suitably against hemipteran, dipteran, blattodean and/or lepidopteran insects. Plant protection agents are described further hereinabove.

Use as an Insect Control Agent

The present invention provides the use of a compound or composition or combination thereof as described herein as an insect control agent, specifically in methods of increasing mortality in insects, or a method of inhibiting infestation of a plant by insects.

The present invention also provides the use of a compound or composition or combination thereof as described herein as an insect control agent, specifically in methods of increasing hemipteran, dipteran, blattodean and/or lepidopteran insect mortality, or in a method of inhibiting or reducing infestation, or reducing insect load of a plant by insects, suitably by hemipteran, dipteran, blattodean and/or lepidopteran insects.

The present invention also provides the use of a compound or composition or combination thereof as described herein as an insect control agent, specifically by having a biostatic effect on hemipteran, dipteran, blattodean and/or lepidopteran insects, a biocidal effect on hemipteran, dipteran, blattodean and/or lepidopteran insects, and/or a pesticidal effect hemipteran, dipteran, blattodean and/or lepidopteran insects.

"Biostatic (effect)" or "biostatic use", as used herein, includes any effect or use of a compound or composition or combination as described herein (optionally comprised in a biostatic, biocidal, fungicidal or fungistatic composition as defined herein) for controlling, modulating or interfering with the harmful activity of a pest, such as a plant pest or a plant pathogen. Suitably the pest is of hemipteran, dipteran, blattodean and/or lepidopteran insect orders. Suitably including but not limited to inhibiting the growth or activity of the insect, altering the behaviour of the insect, and repelling or attracting the insect in plants, plant parts or in other agro-related settings, such as for example for household uses or in soil.

"Pesticidal activity" or "biocidal activity", as used interchangeably herein, means killing the pest or severely disabling the pest. Suitably which may be the same as insecticidal activity wherein the pest is an insect. Suitably, the compound, composition or combination may be for use as an insect control agent wherein the insect encodes a kinin peptide.

Suitably, the compound or composition or combination may be for use as an insect control agent wherein the insect is of the order diptera. Suitably, the compound may be for use as an insect control agent wherein the insect is of the genus *Drosophila*. Suitably, the compound may be for use as an insect control agent wherein the insect is *Drosophila suzukii*.

Suitably, the compound or composition or combination as defined herein may be for use as an insect control agent wherein the insect is of the order hemiptera. Suitably, the compound or composition or combination as defined herein may be for use as an insect control agent wherein the insect is an aphid. Suitably, the compound or composition or combination as defined herein may be for use as an insect control agent wherein the insect is of the genus *Myzus*. Suitably, the compound or composition or combination as defined herein may be for use as an insect control agent wherein the insect is *Myzus persicae*.

Suitably, the compound or composition or combination as defined herein may be for use as an insect control agent wherein the insect is of the order hemiptera. Suitably, the compound or composition or combination as defined herein may be for use as an insect control agent wherein the insect is of the genus *Halyomorpha*. Suitably, the compound or composition or combination as defined herein may be for use as an insect control agent wherein the insect is *Halyomorpha halys*.

Suitably, the compound or composition or combination as defined herein may be for use as an insect control agent wherein the insect is of the order lepidoptera. Suitably, the compound or composition or combination as defined herein may be for use as an insect control agent wherein the insect is of the genus *Plutella*. Suitably, the compound or composition or combination as defined herein may be for use as an insect control agent wherein the insect is *Plutella xylostella*.

Suitably, the compound or composition or combination as defined herein may be for use as an insect control agent wherein the insect is of the order lepidoptera. Suitably, the compound or composition or combination as defined herein may be for use as an insect control agent wherein the insect is of the genus *Spodoptera*. Suitably, the compound or composition or combination as defined herein may be for use as an insect control agent wherein the insect is *Spodoptera frugiperda.*

Suitably, the compound or composition or combination as defined herein may be for use as an insect control agent wherein the insect is of the order blattodea. Suitably, the compound or composition or combination as defined herein may be for use as an insect control agent wherein the insect is a cockroach or a termite.

Methods of Controlling Insect Fecundity

The present invention also provides insecticidal compounds, compositions and combinations as described herein for controlling fecundity of insect species. Suitably, the insect is selected from hemipteran, dipteran, blattodean or lepidopteran insects, such as those described anywhere herein. Suitably wherein in some embodiments the hemipteran insect is *Myzus persicae*. Suitably wherein in some embodiments the dipteran insect is *D. suzukii*. Suitably wherein in some embodiments the lepidopteran insect is *Plutella xylostella*. Suitably wherein in some embodiments the lepidopteran insect is *Spodoptera frugiperda.*

There is also provided a method of controlling fecundity of an hemipteran insect, the method comprising contacting a compound of the invention, or a composition of the invention to a substrate, e.g. a plant or soil. Suitably, the hemipteran insect is any of those disclosed herein, e.g., an aphid.

There is also provided a method of controlling fecundity of a dipteran insect, the method comprising contacting a compound of the invention, or a composition of the invention to a substrate, e.g. a plant or soil. Suitably, the dipteran insect is any of those disclosed herein.

There is also provided a method of controlling fecundity of an lepidopteran insect, the method comprising contacting a compound of the invention, or a composition of the invention to a substrate, e.g. a plant or soil. Suitably, the lepidopteran insect is any of those disclosed herein.

There is also provided a method of controlling fecundity of a blattodean insect, the method comprising contacting a compound of the invention, or a composition of the invention to a substrate, e.g. a plant or soil. Suitably, the blattodean insect is any of those disclosed herein. Suitably, the combination comprises a compound of the invention, and a further kinin peptide, or an analogue thereof.

There is also provided a method of controlling fecundity of a hemipteran insect, the method comprising contacting a combination as described herein, to a substrate, e.g. a plant or soil. Suitably, the hemipteran insect is any of those disclosed herein. Suitably, the combination comprises a compound of the invention, and a further kinin peptide, or an analogue thereof.

There is also provided a method of controlling fecundity of a dipteran insect, the method comprising contacting a combination as described herein, to a substrate, e.g. a plant or soil. Suitably, the dipteran insect is any of those disclosed herein. Suitably, the combination comprises a compound of the invention, and a further kinin peptide, or an analogue thereof.

There is also provided a method of controlling fecundity of a lepidopteran insect, the method comprising contacting a combination as described herein, or a composition of the invention to a substrate, e.g. a plant or soil. Suitably, the lepidopteran insect is any of those disclosed herein. Suitably, the combination comprises a compound of the invention, and a further kinin peptide, or an analogue thereof.

There is also provided a method of controlling fecundity of a blattodean insect, the method comprising contacting a combination as described herein, or a composition of the invention to a substrate, e.g. a plant or soil. Suitably, the blattodean insect is any of those disclosed herein. Suitably, the combination comprises a compound of the invention, and a further kinin peptide, or an analogue thereof.

There is also provided a method of controlling fecundity of an hemipteran insect or insect population, the method comprising contacting a compound of the invention, or a composition of the invention to an hemipteran insect or insect population. Suitably, the hemipteran insect is any of those disclosed herein.

There is also provided a method of controlling fecundity of a dipteran insect or insect population, the method comprising contacting a compound of the invention, or a composition of the invention to a dipteran insect or insect population. Suitably, the dipteran insect is any of those disclosed herein.

There is also provided a method of controlling fecundity of a lepidopteran insect or insect population, the method comprising contacting a compound of the invention, or a composition of the invention to a lepidopteran insect or insect population. Suitably, the lepidopteran insect is any of those disclosed herein.

There is also provided a method of controlling fecundity of a blattodean insect or insect population, the method comprising contacting a compound of the invention, or a composition of the invention to a blattodean insect or insect population. Suitably, the blattodean insect is any of those disclosed herein.

There is also provided a method of controlling fecundity of a hemipteran insect or insect population, the method comprising contacting a combination as described herein, to a hemipteran insect or insect population. Suitably, the hemipteran insect is any of those disclosed herein. Suitably, the combination comprises a compound of the invention, and a further kinin peptide, or an analogue thereof.

There is also provided a method of controlling fecundity of a dipteran insect or insect population, the method comprising contacting a combination as described herein, to a dipteran insect or insect population. Suitably, the dipteran insect is any of those disclosed herein. Suitably, the combination comprises a compound of the invention, and a further kinin peptide, or an analogue thereof.

There is also provided a method of controlling fecundity of a lepidopteran insect or insect population, the method comprising contacting a combination as described herein, or a composition of the invention to a lepidopteran insect or insect population. Suitably, the lepidopteran insect is any of those disclosed herein. Suitably, the combination comprises a compound of the invention, and a further kinin peptide, or an analogue thereof.

There is also provided a method of controlling fecundity of a blattodean insect or insect population, the method comprising contacting a combination as described herein, or a composition of the invention to a blattodean insect or insect population. Suitably, the blattodean insect is any of those disclosed herein. Suitably, the combination comprises a compound of the invention, and a further kinin peptide, or an analogue thereof.

In the context of the present invention, "controlling fecundity" refers to reducing, inhibiting, or eliminating the presence of an insect species during one or more of its growth stages. For example, the compositions of the present invention may be used for controlling the growth of mites at any stage such as egg, larva, nymph, and adult form.

Combinations with Further Insecticides

The compound of the invention may be used in combination with one or more further insecticides or insecticidal compounds, such as those as described herein. There is also provided a combination comprising a compound of the invention, or a salt or solvate thereof, in combination with one or more additional active insecticides, or insecticidal compounds.

The composition of the invention may further comprise one or more additional active insecticides, or active insecticidal compounds.

Suitably, the insecticide may be selected from an insect neuropeptide or analogues thereof such as a kinin peptide, an AKH peptide, a DH31 peptide, a DH44 peptide, a pyrokinin peptide or a CAPA peptide (e.g. a CAPA-1, CAPA-2 or CAPA-3 analogue). In a particular embodiment, the further insecticide is a further kinin peptide, for example SB-P-69 ([Hy]-NFSPWG-[$NH_2$], SEQ ID NO:14). Additionally or alternatively, the insecticide may be selected from a chemical insecticide, such as: Pyrethroids (Permethrin, Cypermethrin, Deltamethrin); Organophosphates (Malathion, Chlorpyrifos, Diazinon); Neonicotinoids (Imidacloprid, Clothianidin, Thiamethoxam); Carbamates (Carbaryl, Methomyl, Propoxur); Botanical Insecticides (Pyrethrin (derived from chrysanthemum flowers), Rotenone (derived from certain plant roots)); Biopesticides (*Bacillus thuringiensis* (Bt) products, *Beauveria bassiana* (fungus), *Metarhizium anisopliae* (fungus)); Insect Growth Regulators (IGRs) (Methoprene, Pyriproxyfen); Fipronil; Spinosad; Avermectins (including abamectin and ivermectin); Chitin Synthesis Inhibitors (Diflubenzuron, Hexaflumuron); Piperonyl Butoxide; Flonicamid; Indoxacarb; and Sulfoxaflor.

Suitably said further insecticides or insecticidal compounds may be comprised in a composition of the invention.

The methods of the invention may further comprise contacting the insect population or plant or part thereof with a further insecticide agent, or insecticidal compound, such as those described herein. Suitably, the further insecticide or insecticidal compound is a kinin peptide.

Suitably any references herein to the compound of the invention or a composition thereof may equally refer to a combination of a compound of the invention with one or more insecticides or insecticidal compounds, or a composition containing such a combination.

Suitably, there is provided a combination comprising a compound of the invention, or a salt or solvate thereof, in combination with one or more of the peptides listed in the table below:

| Family | Peptide | Sequence | SEQ ID NO. |
|---|---|---|---|
| Pyrokinin | SB-P-46 | [Hy]-SPPYSPPFSPRL-[$NH_2$] | 8 |
| | SB-P-47 | [Pyr]-AIMARPQVPRL-[$NH_2$] | 3 |
| | SB-P-48 | Hy-EQNVQSNGEPAYRVRTPRL-[$NH_2$] | 15 |
| | SB-P-49 | [Hy]-SVPFKPRL-[$NH_2$] | 4 |
| | SB-P-51 | [Hy]-LRQLQSNGEPAYRVRTPRL-[$NH_2$] | 5 |
| | SB-P-80 | [Hy]-NADEDQQQSVDFTPRL-[$NH_2$] | 6 |
| | SB-P-81 | [Hy]-GGSMTFSPRL-[$NH_2$] | 7 |
| Kinin | SB-P-65 | [Hy]-RQKTVFSSWG-[$NH_2$] | 9 |
| | SB-P-66 | [Hy]-PAFSSWG-[$NH_2$] | 10 |
| | SB-P-69 | [Hy]-NFSPWG-[$NH_2$] | 14 |

-continued

| Family | Peptide | Sequence | SEQ ID NO. |
|---|---|---|---|
| AKH | SB-P-86 | [Pyr]-LTFTSSWGG-[$NH_2$] | 11 |
| | SB-P-39 | [Palm]-QLTFSPDW-[$NH_2$] | 12 |
| | SB-P-41 | Hy-QLTFSPDW-[$NH_2$] | 16 |
| | SB-P-42 | [Pyr]-LTFSPDW-[$NH_2$] | 13 |

In one embodiment, the compound of the invention is utilised in combination with a pyrokinin peptide. e.g.

| Family | Peptide | Sequence | SEQ ID NO. |
|---|---|---|---|
| Pyrokinin | SB-P-46 | [Hy]-SPPYSPPFSPRL-[$NH_2$] | 8 |
| | SB-P-47 | [Pyr]-AIMARPQVPRL-[$NH_2$] | 3 |
| | SB-P-48 | Hy-EQNVQSNGEPAYRVRTPRL-[$NH_2$] | 15 |
| | SB-P-49 | [Hy]-SVPFKPRL-[$NH_2$] | 4 |
| | SB-P-51 | [Hy]-LRQLQSNGEPAYRVRTPRL-[$NH_2$] | 5 |
| | SB-P-80 | [Hy]-NADEDQQQSVDFTPRL-[$NH_2$] | 6 |
| | SB-P-81 | [Hy]-GGSMTFSPRL-[$NH_2$] | 7 |

In one embodiment, the compound of the invention is utilised in combination with a further kinin peptide, e.g.

| Family | Peptide | Sequence | SEQ ID NO. |
|---|---|---|---|
| Kinin | SB-P-65 | [Hy]-RQKTVFSSWG-[$NH_2$] | 9 |
| | SB-P-66 | [Hy]-PAFSSWG-[$NH_2$] | 10 |
| | SB-P-69 | [Hy]-NFSPWG-[$NH_2$] | 14 |

In one embodiment, the compound of the invention is utilised in combination with a CAPA peptide (e.g. a CAPA2 peptide).

In one embodiment, the compound of the invention is utilised in combination with an AKH peptide, e.g.

| Family | Peptide | Sequence | SEQ ID NO. |
|---|---|---|---|
| AKH | SB-P-86 | [Pyr]-LTFTSSWGG-[$NH_2$] | 11 |
| | SB-P-39 | [Palm]-QLTFSPDW-[$NH_2$] | 12 |
| | SB-P-41 | Hy-QLTFSPDW-[$NH_2$] | 16 |
| | SB-P-42 | [Pyr]-LTFSPDW-[$NH_2$] | 13 |

Suitably any of the above combinations of compounds may be comprised within a composition of the invention.

The choice of ancillary or additional insecticides will typically depend on the particular target species.

Beneficial Insect Species

The compounds and compositions and combinations of the invention may be substantially non-toxic to beneficial insect species, including species which prey on pests and pollinator species. Important pollinator species, such as insects of the superfamily Apoidea, including bees, such as the Apidae, e.g. those of the genus *Bombus*, such as *Bombus terrestris*. Important predatory species include Coccinellidae (lady bugs) such as *Adalia bipunctata*.

By substantially non-toxic, it is meant that the compounds and compositions and combinations of the invention do not cause death of the beneficial insect species (e.g. pollinator species), suitably that they do not cause premature death of the beneficial insect species (e.g. pollinator species). It is also meant that the compounds and compositions and combinations of the invention do not cause any detrimental side effects to the beneficial insect species (e.g. pollinator species), for example they do not have a negative effect on feeding behaviour, or ability to move.

Compositions

The present inventors have provided compositions comprising at least one insecticidal compound or combination thereof of the invention, which can specifically bind to an insect. Importantly, through this interaction with a specific molecular structure of the insect, such as a receptor, suitably a neurological receptor, the compositions disclosed herein are capable of inhibiting, preventing or reducing one or more biological activities of the insect, such that the growth or fecundity of the insect is inhibited, prevented or reduced. In certain embodiments, the compositions as disclosed herein are capable of killing insects through the specific interaction of at least one insecticidal compound, which can specifically bind to an insect receptor, and which is comprised in the compositions.

Compositions of the invention, or for use in accordance with the invention, typically comprise a compound as described in combination with one or more ancillary component such as solvents, carriers, diluents, adjuvants, preservatives, dispersants, emulsifying agents, or synergists. Suitably the composition may be an agricultural composition, an insect control composition (e.g. insecticide composition), or a plant protection composition.

In any of these embodiments, the compound or combination of compounds of the invention may be provided as part of a composition, such as an agricultural composition, an insect control composition (e.g. insecticide composition) or a plant protection composition. Reference to application or use of a compound or combination herein should therefore be construed as encompassing application or use of a suitable composition thereof, unless the context demands otherwise.

The composition typically comprises a compound as described herein in admixture with one or more ancillary component such as solvents, carriers, diluents, adjuvants, preservatives, dispersants, emulsifying agents, or synergists.

The composition may further comprise a combination with one or more additional active insecticides as described herein.

The invention further provides a composition, e.g. an agricultural composition, an insect control composition or plant protection composition, comprising a compound of the invention, or a combination thereof, in admixture with one or more solvents, carriers, diluents, adjuvants, preservatives, dispersants, emulsifying agents, or synergists. The composition may be an aqueous composition. Further details of which are explained hereinbelow.

"Agricultural", as used herein, means suitable for use in the agricultural or agrochemical industry, including horticulture, floriculture and home and garden uses, but also products intended for non-crop related uses such as public health/pest control operator uses to control undesirable insects and rodents, household uses, such as household fungicides and insecticides and agents, for protecting plants or parts of plants, crops, bulbs, tubers, fruits (e.g. from harmful organisms, diseases or pests); for controlling, preferably promoting or increasing, the growth of plants; and/or for promoting the yield of plants, crops or the parts of plants that are harvested (e.g. its fruits, flowers, seeds etc.). Examples of such substances will be clear to the skilled person and preferably in the context of the present invention, include compounds that are active as insecticides (e.g. contact insecticides or systemic insecticides, including insecticides for household use). Other such agrochemicals may be pesticides, growth regulators, nutrients/fertilizers, repellants, defoliants etc.

"Agricultural use", as used herein, not only includes the use of the insecticidal compounds of the invention, combinations thereof or compositions, and optionally the agrochemicals as defined above (for example, pesticides, growth regulators, nutrients/fertilizers, repellants, defoliants etc.), that are suitable and/or intended for use in field grown crops (e.g., agriculture), but also includes the use of compounds of the invention combinations thereof or compositions and said agrochemicals as defined above that are meant for use in greenhouse grown crops (e.g. horticulture/floriculture) or hydroponic culture systems and even the use of compounds combinations thereof or compositions of the invention and agrochemicals as defined above that are suitable and/or intended for non-crop uses such as uses in private gardens, household uses (for example, herbicides or insecticides for household use), or uses by pest control operators (for example, weed control etc.).

Suitably an insect control composition according to the invention is for controlling insect populations. Formulations of such compositions for controlling insect populations are known to the person skilled in the art and include, but are not limited to liquid emulsifiable concentrates, wettable powders, solutions, suspension concentrates, emulsions, suspoemulsions, granules and water dispersible granules (Mulqueen, 2003). Preferably, said insect control compositions according to the invention comprise an insecticidal compound of the invention, and optionally a combination of further insecticidal compounds. Suitably said insecticidal compound is comprised in a carrier as described hereinbelow.

Compositions of the invention may comprise a pesticide formulation or an agrochemical formulation. A "pesticide formulation" as used herein means any composition comprising a compound or combination of compounds intended for preventing, destroying, repelling, attracting or mitigating any pest. An "agrochemical formulation" as used herein means a composition for agricultural use, comprising a biologically active agent, optionally with one or more additives favoring optimal dispersion, atomization, distribution, retention and/or activity of agrochemicals. As a non-limiting example such additives are diluents, solvents, adjuvants, surfactants, wetting agents, spreading agents, oils, stickers, penetrants, buffering agents, acidifiers, defoaming agents or drift control agents.

A composition as used herein means a composition comprising at least one active substance, suitably an insecticidal compound of the invention, optionally with one or more additives favouring optimal dispersion, atomization, deposition, leaf wetting, distribution, retention and/or uptake of said active substance. It will become clear from the further description herein that a composition as used herein includes biological insect control agents or biological insecticides, and these terms will be interchangeably used in the present application. Accordingly, a composition as used herein includes compositions comprising at least one biological molecule as an active ingredient, substance or principle for controlling pests in plants or in other agro-related settings (such for example in soil). Suitably wherein the at least one biological molecule comprises an insecticidal compound of the invention or a combination thereof. Suitably wherein the pest is an insect. As a non-limiting example, the additives in the compositions disclosed herein may include but are not limited to diluents, solvents, adjuvants, surfactants, wetting agents, spreading agents, oils, stickers, thickeners, penetrants, buffering agents, acidifiers, antisettling agents, antifreeze agents, photo-protectors, defoaming agents, biocides and/or drift control agents.

Suitably, the compositions of the invention are aqueous compositions.

The compound content of the composition can vary within wide limits. The compound concentration of the composition is suitably an effective amount, and can be from 0.0000001 to 95% by weight of the compound, preferably between 0.0001 and 1% by weight. The terms "effective amount" and "effective dose", as used herein, mean the amount needed to achieve the desired result or results.

In a specific embodiment the concentration of the compound of the invention contained in the composition may be at least 0.0001% by weight. In a specific embodiment the concentration of the compound of the invention contained in the composition may be up to 50% by weight. In a specific embodiment the concentration of the compound of the invention contained in the composition may be from 0.0001% to 50% by weight. In particular embodiments, the present invention provides compositions comprising at least one insecticidal compound of the invention, wherein the concentration of the at least one compound of the invention in the composition ranges from 0.001% to 50% by weight. In yet another specific embodiment the concentration of the at least one compound of the invention contained in the composition may be from 0.001% to 50% by weight. In yet another specific embodiment the concentration of the at least one compound of the invention contained in the composition may be from 0.01% to 50% by weight. In yet another specific embodiment the concentration of the at least one compound of the invention contained in the composition may be from 0.1% to 50% by weight.

The compositions of the invention, or for use in accordance with the invention, may comprise more than one compound of the invention in combination, and/or with other insecticidal compounds as described herein in combination. Therefore the compositions of the invention may comprise a first compound of the invention and a second compound of the invention, or a first compound of the invention and a second insecticidal compound, for example. Suitably the first and second compound may be any of those described herein, and may be present in the composition in any relative proportion.

The composition may be an aqueous composition, e.g. a saline composition. The aqueous composition may contain one or more buffers, such as a phosphate buffer (e.g. phosphate buffered saline) or a Tris buffer. Alternatively the composition may be an oil dispersion or an emulsion, e.g. an oil and water emulsion. Alternatively the composition may be a suspension, powder, foam, paste, granule, aerosol, impregnated natural and synthetic substance, or encapsulated in polymeric substance for example. A suitable form of the composition may be chosen for the intended use having regard to the target insect, and to its habitat.

Adjuvants may enhance product performance, for example, by increasing the efficiency of the delivery of active ingredients, reducing the level of active ingredient required, or extending the spectrum of effectiveness.

Different types of adjuvants offer various benefits and advantages, which are achieved by modulating properties such as spray formation, spray retention, wetting, deposit formation or uptake.

Adjuvants modulating spray formation may influence spray quality by reducing spray drift and wastage, allowing more of the product to reach the target. This can reduce use rates, leading to a better environmental profile and a potentially more cost effective solution. Such adjuvants include non-ionic surfactants and emulsifier blends.

Adjuvants modulating spray retention may dissipate the kinetic energy of the droplet during impact, meaning the likelihood of bounce or run-off is reduced. Such adjuvants include alkyl polyglucosides, alkoxylated alcohols, and polyoxyethylene monobranched alcohols (e.g. polyoxyethylene (8) monobranched alcohol).

Adjuvants modulating wetting properties (i.e. wetting agents) may reduce surface tension and contact angle, leading to enhanced coverage. Such adjuvants include polyoxyethylene sorbitan monolaurate (e.g. polyoxyethylene (8) sorbitan monolaurate), surfactant blends, and alkyl polyglucosides.

Adjuvants modulating deposit formation may influence evaporation of water from the droplet and thus provide a more homogeneous distribution. Such adjuvants include alkoxylated polyol esters, polyoxyethylene sorbitan monolaurate (e.g. polyoxyethylene (12) sorbitan monolaurate), and alkyl polyglucoside.

Adjuvants modulating uptake can improve penetration and uptake of active ingredients. e.g. through the insect cuticle, resulting in increased bioavailability. Such adjuvants include alkoxylated polyol esters and polyoxyethylene sorbitan monolaurate (e.g. polyoxyethylene (12) sorbitan monolaurate and polyoxyethylene (16) sorbitan monolaurate).

Dispersants may be aqueous or non-aqueous. An oil dispersion (OD) formulation typically comprises a solid active ingredient dispersed in oil. The oil can vary from paraffinic to aromatic solvent types and vegetable oil or methylated seed oils. Typically the active ingredient is uniformly suspended in the oil phase. Although primarily used for water sensitive active ingredients, OD formulations have extended to other active ingredients due to their better spray retention, spreading, foliar uptake, and penetration enhancement (e.g. across the insect cuticle) as the carrier oil often acts as an adjuvant.

Oils suitable for use in OD dispersions include linseed, rapeseed and soyabean oils.

Aqueous dispersants may be used, for example, to improve stability in the spray tank after dilution in water, and may include modified styrene acrylic polymers, and polymeric amphoteric dispersants and adjuvants.

An emulsifier may be employed to emulsify a continuous oil phase into water when an OD formulation is diluted prior to being sprayed. The emulsifier may be selected based upon its ability to spontaneously form the emulsion. Their performance is primarily dictated by the nature of the surfactant and their collective effect on how they arrange themselves at the oil/water interface. Examples include polyoxyethylene sorbitol hexaoleate (e.g. polyoxyethylene (40) sorbitol hexaoleate), emulsifier blends, and calcium alkylaryl sulphonate.

The composition may further comprise an adhesive or a dye.

The compound may be provided in the form of a concentrate, for dilution prior to application. Alternatively the compound may be provided in a solid form to be suspended or dissolved prior to formulation.

The compositions as disclosed herein are themselves in fairly diverse, solid or liquid, forms. As solid composition forms, there may be mentioned dustable powders (content of active substance which may be up to 100%) and granules, in particular those obtained by extrusion, by compacting, by impregnation of a granulated carrier, by granulation using a powder as starting material (the content of active substance in these granules being between 0.5 and 80% for these latter cases). Such solid compositions may be optionally used in the form of a liquid which is viscous to a greater or lesser degree, depending on the type of application desired, for example by diluting in water. As liquid composition forms or forms intended to constitute liquid compositions during application, there may be mentioned solutions, in particular water-soluble concentrates, emulsions, suspension concentrates, wettable powders (or spraying powder), oils and waxes. The suspension concentrates, which can be applied by spraying, are prepared so as to obtain a stable fluid product which does not form a deposit and they usually contain from 10 to 75% of active substance, from 0.5 to 15% of surfactants, from 0.1 to 10% of thixotropic agents, from 0 to 10% of appropriate additives, such as antifoams, corrosion inhibitors, stabilizers, penetrating agents and adhesives and, as carrier, water or an organic liquid in which the active substance is not or not very soluble: some organic solids or inorganic salts may be dissolved in the carrier to help prevent sedimentation or as antigels for water.

A "carrier", as used herein, means any solid, semi-solid or liquid carrier in or on(to) which an active substance, such as the insecticidal compounds or combinations of the invention, can be suitably incorporated, included, immobilized, adsorbed, absorbed, bound, encapsulated, embedded, attached, or comprised. Non-limiting examples of such carriers include nanocapsules, microcapsules, nanospheres, microspheres, nanoparticles, microparticles, liposomes, vesicles, beads, a gel, weak ionic resin particles, liposomes, cochleate delivery vehicles, small granules, granulates, nano-tubes, bucky-balls, water droplets that are part of an water-in-oil emulsion, oil droplets that are part of an oil-in-water emulsion, organic materials such as cork, wood or other plant-derived materials (e.g. in the form of seed shells, wood chips, pulp, spheres, beads, sheets or any other suitable form), paper or cardboard, inorganic materials such as talc, clay, microcrystalline cellulose, silica, alumina, silicates and zeolites, or even microbial cells (such as yeast cells) or suitable fractions or fragments thereof.

In one embodiment, the carrier is a liposome. In one embodiment, the composition of the invention comprises one more liposomes suitably wherein each liposome comprises a compound of the invention, or combination thereof. Suitably therefore the invention provides a composition or formulation comprising a plurality of liposomes, said liposomes comprising a compound of the invention, or a combination thereof. Suitably the liposomes comprise a lipid component, suitably which may be soy lecithin and glycerol. Suitably the liposomes are formed of soy lecithin and glycerol. Suitably the liposomes are formed of 25 mg/ml of glycerol and 3% glycerol. Suitably the liposomes comprise an effective concentration of the compound of the invention. Suitably the liposomes comprise around $10^{-4}$ M of a compound of the invention, or a combination thereof. Suitably therefore the invention provides a composition or formulation comprising a plurality of liposomes, said liposomes comprising a compound of the invention, or a combination thereof, soy lecithin (preferably 25 mg/ml) and glycerol (preferably 3%).

Suitably the liposomes may be manufactured by the Mozafari Heating Method (Mozafari, M. R. "Nanoliposomes: preparation and analysis." *Liposomes: Methods and Protocols, Volume* 1: *Pharmaceutical Nanocarriers* (2010): 29-50. Suitably such a method comprises (a) admixing the compound of the invention with glycerol, suitably with a 50% glycerol solution, (b) admixing the mixture of step (a) with soy lecithin, suitably with 350 mg of soy lecithin in an aqueous solution, (c) heating the mixture of step (b) whilst stirring to form liposomes, suitably at around 60 °C and at around 800 RPM for around 40 minutes, (d) annealing the liposomes, suitably by placing in 40 °C water for around 1-2 hours, and (e) sonicating the liposomes, suitably for around 30 minutes in a sonicator bath.

Suitably the liposomes have an average diameter of around 150 to 250 nm, suitably around 175 nm to 225 nm, suitably around 190 nm to 210 nm, suitably around 200 nm. Suitably the size of the liposomes is determined by using Dynamic light scattering (DLS), for example using a Malvern Zetasizer Nano. Suitably the liposomes have a polydispersity index of between 0.25 to 0.35, suitably 0.26 to 0.33, suitably 0.26 to 0.31, suitably 0.26 to 0.30, suitably 0.26 to 0.29, suitably 0.26 to 0.28, suitably around 0.26.

In the compositions of the invention, the carrier with the one or more insecticidal compounds may for example be maintained as a wettable powder, wettable granule, emulsifiable concentrate, suspension concentrate, microemulsion, capsule suspension, dry microcapsule, tablet or gel or be suspended, dispersed, emulsified or otherwise brought in a suitable liquid medium (such as water or another suitable aqueous, organic or oily medium) so as to provide a (concentrated) liquid composition of the invention that has a stability that allows the composition of the invention to be suitably stored or (where necessary after further dilution) applied to the intended site of action. Suitably the composition of the invention can be transported and/or stored prior to final use, optionally (and usually preferably) as a suitable liquid concentrate, dry powder, tablet, capsule suspension, slurry or "wet cake", which can be suitably diluted, dispersed, suspended, emulsified or otherwise suitably reconstituted by the end user prior to final use. The composition of the invention allows to be applied to the intended site of action using any suitable or desired manual or mechanical technique such as spraying, pouring, dripping, brushing, coating, dripcoating, applying as small droplets, a mist or an aerosol or any other suitable technique. In one embodiment, said intended site of action is an intact living insect, even more preferably an insect surface.

The composition may be a bait composition for ingestion by the target insect. A bait composition may comprise one or more phagostimulants, i.e. a substance which will entice the insect to ingest the compound. Phagostimulants may include artificial sweeteners, amino acids, other peptides or proteins and carbohydrates (e.g. glucose, fructose, sucrose, maltose) etc. Examples include honey, syrups and aqueous solutions of sucrose.

Commercially available base formulations may also be suitable for use in formulating the compounds described in this specification, such as Armid® FMPC (Akzo Nobel).

The composition may comprise one or more synergists, i.e. compounds which increase the efficacy of insecticides against their targets, often by inhibiting an insect's ability to metabolise the active agent. Common synergists include piperonyl butoxide and MGK-264 (n-octyl bicycloheptane dicarboximide), or peptidase inhibitors.

The composition may comprise one or more agents which promote stability of the insecticidal compounds of the invention. Suitably the one or more agents which promote stability may prevent degradation of the insecticidal compounds of the invention. Suitable agents which prevent degradation of the insecticidal compounds of the invention may inhibit or reduce the activity of enzymes, suitably of enzymes which act to degrade proteins, suitably proteases, for example. Suitably therefore the composition may comprise one or more protease inhibitors, suitably which may be selected from: Bowman-Birk Inhibitors, Kunitz Inhibitors, Cystatin, Trypsin Inhibitors, Serpins, Tannins, Proteinase Inhibitor-II (PI-II), and Alpha-AI1.

The composition may further comprise one or more additional, attractants, sterilizing agents, acaricides, nematicides, fungicides, growth-regulating substances or herbicides.

In some embodiments, the compositions may comprise one or more further agricultural chemicals or agrochemicals such as herbicides (e.g. contact herbicides or systemic herbicides, including herbicides for household use), fungicides (e.g. contact fungicides or systemic fungicides, including fungicides for household use), nematicides (e.g. contact nematicides or systemic nematicides, including nematicides for household use) and other pesticides or biocides (for example agents for killing insects or snails); as well as fertilizers; growth regulators such as plant hormones; micronutrients, safeners, pheromones; repellants; insect baits; and/or active principles that are used to modulate (i.e. increase, decrease, inhibit, enhance and/or trigger) gene expression (and/or other biological or biochemical processes) in or by the targeted plant (e.g. the plant to be protected or the plant to be controlled), such as nucleic acids (e.g., single stranded or double stranded RNA, as for example used in the context of RNAi technology) and other factors, proteins, chemicals, etc. known per se for this purpose, etc.

Examples of such agrochemicals will be clear to the skilled person; and for example include, without limitation: glyphosate, paraquat, metolachlor, acetochlor, mesotrione, 2,4-D,atrazine, glufosinate, sulfosate, fenoxaprop, pendimethalin, picloram, trifluralin, bromoxynil, clodinafop, fluroxypyr, nicosulfuron, bensulfuron, imazetapyr, dicamba, imidacloprid, thiamethoxam, fipronil, chlorpyrifos, deltamethrin, lambda-cyhalotrin, endosulfan, methamidophos, carbofuran, clothianidin, cypermethrin, abamectin, diflufenican, spinosad, indoxacarb, bifenthrin, tefluthrin, azoxystrobin, thiamethoxam, tebuconazole, mancozeb, cyazofamid, fluazinam, pyraclostrobin, epoxiconazole, chlorothalonil, copper fungicides, trifloxystrobin, prothioconazole, difenoconazole, carbendazim, propiconazole, thiophanate, sulphur, boscalid, chlorantraniliprole and other known agrochemicals or any suitable combination(s) thereof.

Methods of Producing the Insecticidal Compounds

The insecticidal compounds described herein may be produced by any method known in the art for the production of peptides. In one embodiment, the insecticidal compounds may be produced by a chemical method, suitably a chemical synthesis method.

Any suitable chemical method may be used to synthesis the insecticidal compounds of the invention.

Suitably the insecticidal compounds are peptides. Suitably therefore they are synthesised by solid-state peptide synthesis. Suitably such synthesis may be carried out by using commercially available machines such as the Biotage Initiator+ Alstra microwave-assisted peptide synthesiser or the CEM Liberty Prime microwave-assisted peptide synthesiser.

In one embodiment of the present invention, the insecticidal compound is a peptide of the formula: [Hy]-KVKF-SAWG-[$NH_2$] (SEQ ID NO:2). Suitably this peptide may be synthesised by the method defined in the examples. Suitably by the method defined in FIG. 2.

In a further aspect of the invention, there is provided an isolated insecticidal compound produced by a process of the invention. Suitably an isolated insecticidal compound of formula (I) produced by a process of the invention.

In a further aspect of the invention there is provided a method of producing a composition as disclosed herein, at least comprising the steps of: (a) obtaining at least one insecticidal compound of formula (I), and (b) formulating the insecticidal compound into a composition.

In a further aspect of the invention there is provided a method of producing and/or manufacturing a variant of the insecticidal compound of formula (I). Such may comprise the steps of: (i) modifying the peptide Z of formula (I) by adding, replacing or deleting at least one amino acid; (ii) assessing the so created variant for its insecticidal activity and—optionally—at least one property selected from the group consisting of biostability, chemical stability, bioavailability, solubility (including the ability to form stable formulations), producibility, and production costs. Where the insecticidal activity is reduced in comparison to the unmodified peptide Z, repeating the process of steps (i) and (ii) until a variant with improved insecticidal activity is obtained. Where the insecticidal activity is improved in comparison to the unmodified peptide Z, the method may include further steps of manufacturing, isolating and purifying the variant. Screening for insecticidal activity and the other above described properties can be conducted as described below or generally known to the person skilled in the art.

In one embodiment is provided a method for manufacturing a variant of the insecticidal compound of the invention, comprising the steps of:

a) modifying the peptide Z by adding, replacing or deleting at least one amino acid;
b) assessing the ability of the variant for its insecticidal activity and;
c) where the insecticidal activity is reduced in comparison to the insecticidal compound comprising the unmodified peptide Z, repeating the process of steps (a) and (b) until a variant with improved insecticidal activity is obtained;
d) where the insecticidal activity is improved in comparison to the insecticidal compound comprising the unmodified peptide Z, further manufacturing, isolating and purifying the variant.

Suitably the step of obtaining at least one insecticidal compound comprises (a) chemically synthesising the insecticidal compound.

Suitable compositions are described hereinabove. Suitable manufacturing methods for formulating the composition are known in the art and include, but are not limited to, high or low shear mixing, wet or dry milling, drip-casting, encapsulating, emulsifying, coating, encrusting, pilling, extrusion granulation, fluid bed granulation, co-extrusion, spray drying, spray chilling, atomization, addition or condensation polymerization, interfacial polymerization, in situ polymerization, coacervation, spray encapsulation, cooling melted dispersions, solvent evaporation, phase separation, solvent extraction, sol-gel polymerization, fluid bed coating, pan coating, melting, passive or active absorption or adsorption.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

BRIEF DESCRIPTION OF THE FIGURES

Aspects and embodiments of the present invention will now be discussed with reference to the accompanying figures in which.

EXAMPLES

Figure 1:
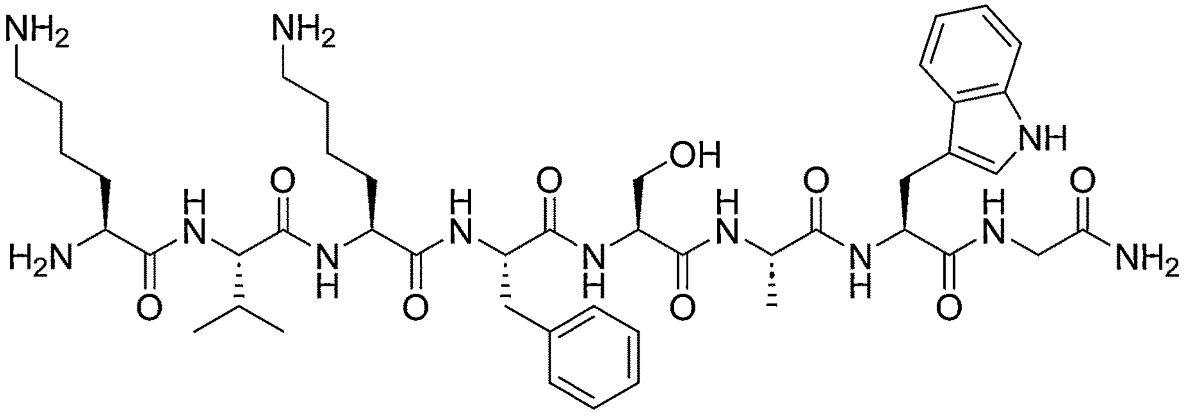
FIG. 1 shows the chemical structure of SB-P-70.

The invention will now be demonstrated and further described by way of the following non-limiting examples.

General Procedures

All amino acids are of L-configuration unless otherwise stated. Standard Fmoc-protected amino acids were purchased from CEM Corporation or Pepceuticals. Suppliers of specialist amino acids are indicated as and when appropriate, as is peptide synthesis resin supplier. Peptide-grade DMF was purchased from Rathburn.

Peptides were synthesised on a Biotage Initiator+Alstra microwave-assisted peptide synthesiser or a CEM Liberty Prime microwave-assisted peptide synthesiser as specified.

High-resolution mass spectrometry (HRMS) was performed on a Bruker microTOF-Q II (ESI+).

Peptides were purified on a reverse-phase Dionex HPLC system equipped with Dionex P680 pumps and a Dionex UVD170U UV-vis detector (monitoring at 214 nm and 280 nm), using a Phenomenex, Gemini, C18, 5 μm, 250×21.2 mm column. Gradients were performed using solvents consisting of A ($H_2O$+0.1% TFA) and B (MeCN+0.1% TFA) and fractions were lyophilised on a Christ Alpha 2-4 LO plus freeze dryer.

Pure peptides were analysed on a Shimadzu reverse-phase HPLC (RP-HPLC) system equipped with Shimadzu LC-20AT pumps, a SIL-20A autosampler and a SPD-20A UV-vis detector (monitoring at 214 nm and 280 nm) using a Phenomenex, Aeris, 5 μm, peptide XB-C18, 150×4.6 mm column at a flow rate of 1 RP-HPLC gradients were run using a solvent system consisting of solution A (100% $H_2O$+0.1% TFA) and B (100% MeCN+0.1% TFA). Typically, two gradients were used to characterise each peptide; a gradient from 5% to 95% solution B over 20 min (incorporating a 2 min hold at 5% solution B and a 5 min wash at 95% solution B at the start and end of the gradient respectively) and a gradient from 5-95% solution B over 50 min (incorporating a 5 min hold at 5% solution B and a 5 min wash at 95% solution B at the start and end of the gradient respectively). In some cases, specialised gradients were used and this is indicated where appropriate. Analytical RP-HPLC data is reported as column retention time (tR) in minutes (min). Analytical columns were maintained at ambient temperature.

LC-MS analysis was performed on a Thermo Scientific LCQ Fleet quadropole mass spectrometer of m/z range 50-2000 Da with an ESI source coupled to a Dionex Ultimate 3000 LC. Analyses were performed on a ReprosilGold 120 C18, 3 μm 150×4 mm column using a linear gradient of buffer A (95/5 $H_2O$/MeCN with 0.1% v/v TFA) to buffer B (95/5 MeCN/$H_2O$ with 0.1% v/v TFA) over 20 min (incorporating a 2 min hold at 0% solution B and a 5 min wash at 100% solution B at the start and end of the gradient respectively). In cases where a specialised analytical RP-HPLC gradient was used to characterise a compound, an analogous LC-MS gradient was used. Analytical RP-HPLC and LC-MS samples were injected as 25 μL of a stock with concentration of 1 mg/mL in $H_2O$/MeCN with 0.1% v/v TFA. LC-MS column oven temperature was maintained at 30 °C.

High-resolution mass spectrometry (HRMS) of pure peptides was performed on a Bruker microTOF-Q II (ESI+).

Proton nuclear magnetic resonance spectra ($^1H$ NMR) for the purpose of peptide content calculations were recorded on an AVANCE III 400 Bruker (400 MHz). Proton chemical shifts are expressed in parts per million (ppm, δ scale) and are referenced to residual protium in the NMR solvent ($CDCl_3$, δ 7.26; $CD_3OD$, δ 3.31 and $D_2O$, δ 4.79). The following abbreviations were used to describe peak patterns when appropriate: br=broad, s=singlet, d=doublet, t=triplet, q=quadruplet, m=multiplet. Coupling constants, J, are reported in Hertz unit (Hz).

General Procedure for Automated Peptide Synthesis

Biotage Initiator+Alstra Synthesiser

Fmoc-protected amino acids were prepared as a 0.2 M (0.1 mmol syntheses), 0.5 M (0.2 mmol syntheses) or 0.7 M (0.5 mmol syntheses) solution in DMF. 5 equivalents of amino acid (relative to the resin loading) were used during coupling cycles. Oxyma and diisopropyl carbodiimide (DIC) were prepared as 0.2 M (0.1 mmol syntheses), 0.5 M (0.2 mmol syntheses) or 0.7 M (0.5 mmol syntheses) solutions in DMF. 5 equivalents of Oxyma and 5 equivalents of DIC (relative to resin loading) were used during coupling cycles. For Fmoc-deprotections, a solution of 20% morpholine (with 5% formic acid) in DMF was used. Coupling reactions were performed under microwave heating at 90 °C for 2 min with the exception of Fmoc-Cys(Trt)-OH, Fmoc-His(Trt)-OH and Fmoc-Arg(PBf)-OH. Coupling of Fmoc-Cys(Trt) and Fmoc-His(Trt)-OH was performed for 10 min at 50 °C. Coupling of Fmoc-Arg(Pbf)-OH was performed for 2 successive cycles (double-coupled) for 2 min at 90 °C. Microwave-assisted Fmoc deprotections were carried out at 90 °C for 1 min.

CEM Liberty Blue Synthesiser

Fmoc-protected amino acids were prepared as a 0.2 M solution in NBP (Tamisolve). 5 equivalents of amino acid (relative to the resin loading) were used during coupling cycles. Oxyma was prepared as a 0.5 M solution in NBP. DIC was prepared as 5 M solution in NBP. 5 equivalents of Oxyma and 5 equivalents of DIC (relative to resin loading) were used during coupling cycles. For Fmoc-deprotections, a solution of 20% pyrrolidine was used. Coupling reactions and Fmoc-deprotections were performed under microwave heating at 90 °C for 2 min and 1 min respectively with the exception of Fmoc-Cys(Trt)-OH, Fmoc-His(Trt)-OH and Fmoc-Arg(Pbf)-OH. Coupling of Fmoc-Cys(Trt) and Fmoc-His(Trt)-OH was performed for 5 min at 50 °C. Coupling of Fmoc-Arg(Pbf)-OH was performed for 2 successive cycles of 5 min at 75 °C.

General Procedure for TFA Cleavage of Peptides

Typically, cleavage tests of peptides were performed by taking ~3 mg of dried resin beads and treating them with TFA/TIS/water (95:2.5:2.5) for 3 h. The filtrate was drained, concentrated and then triturated in cold diethyl ether ($Et_2O$). The triturate was dissolved in acetonitrile/water, then analysed by RP-HPLC/LC-MS.

Peptides were typically cleaved from the resin in bulk by gently rocking the resin at rt in a cleavage cocktail of TFA/TIS/$H_2O$ (95:2.5:2.5) for 3 h before being drained and the TFA blown off with a steady stream of $N_2$ gas. Peptides containing cysteine or tryptophan residues were cleaved from the resin using a cleavage cocktail of TFA/TIS/$H_2$/DODT (94:2.5:1:2.5) for 3 h. In all cases the crude peptide was triturated with cold $Et_2O$. $Et_2O$ was removed from the resulting crude peptide pellet under a steady stream of nitrogen. The crude peptide was then redissolved in $H_2O$/MeCN and purified by RP-HPLC.

Figure 2:
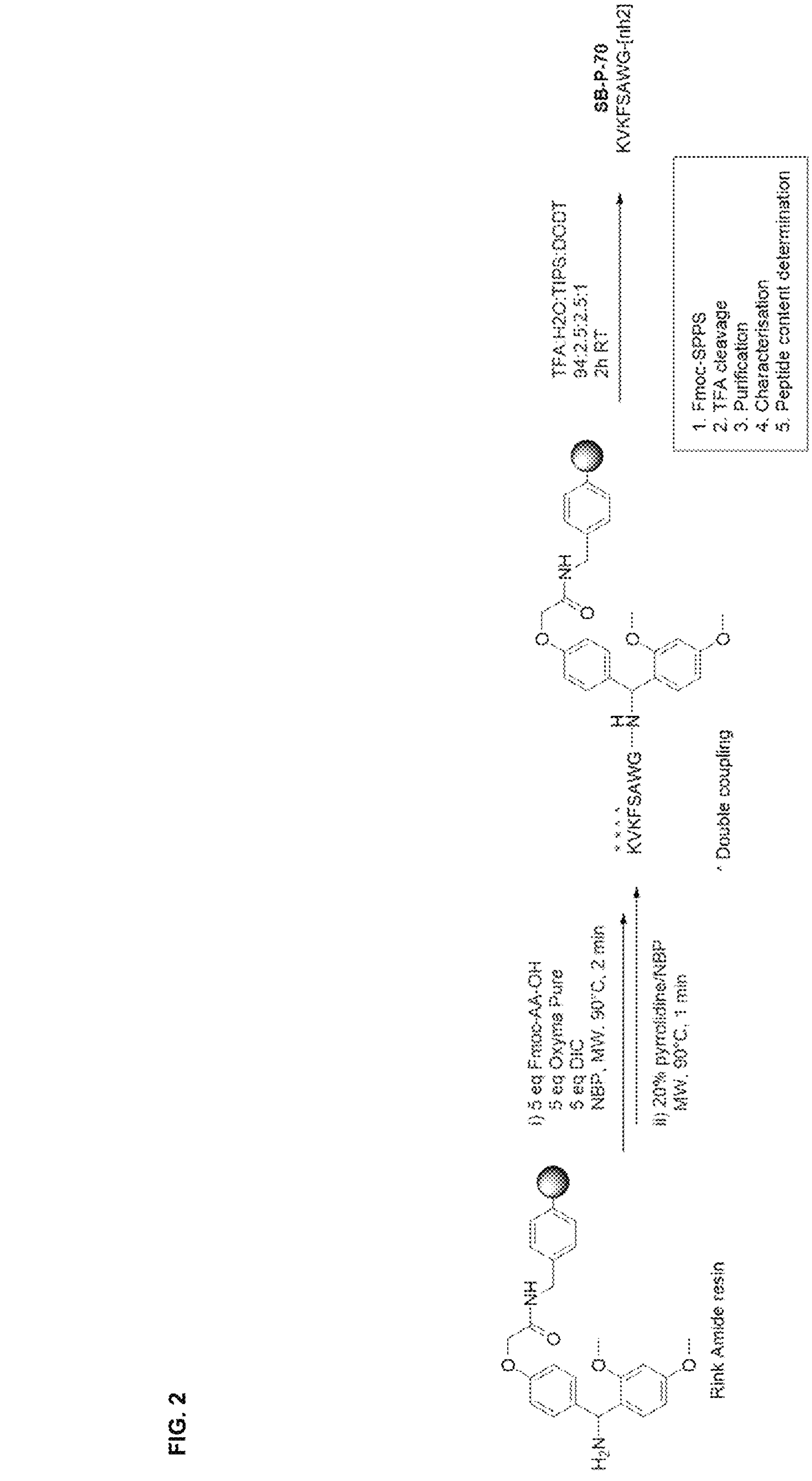
FIG. 2 shows the chemical synthesis route for synthesising SB-P-70.
Figure 3:
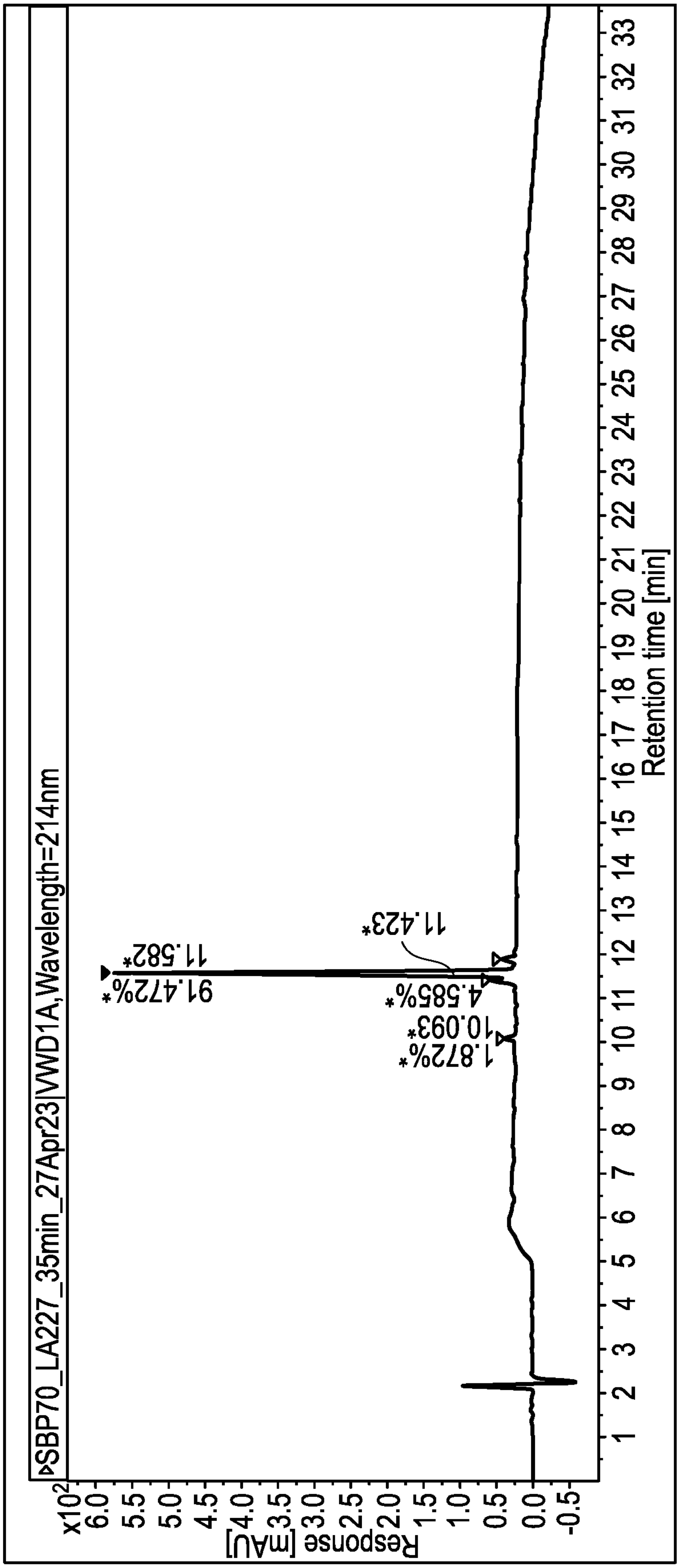
FIG. 3 shows an HPLC trace of SB-P-70.
Figure 4:
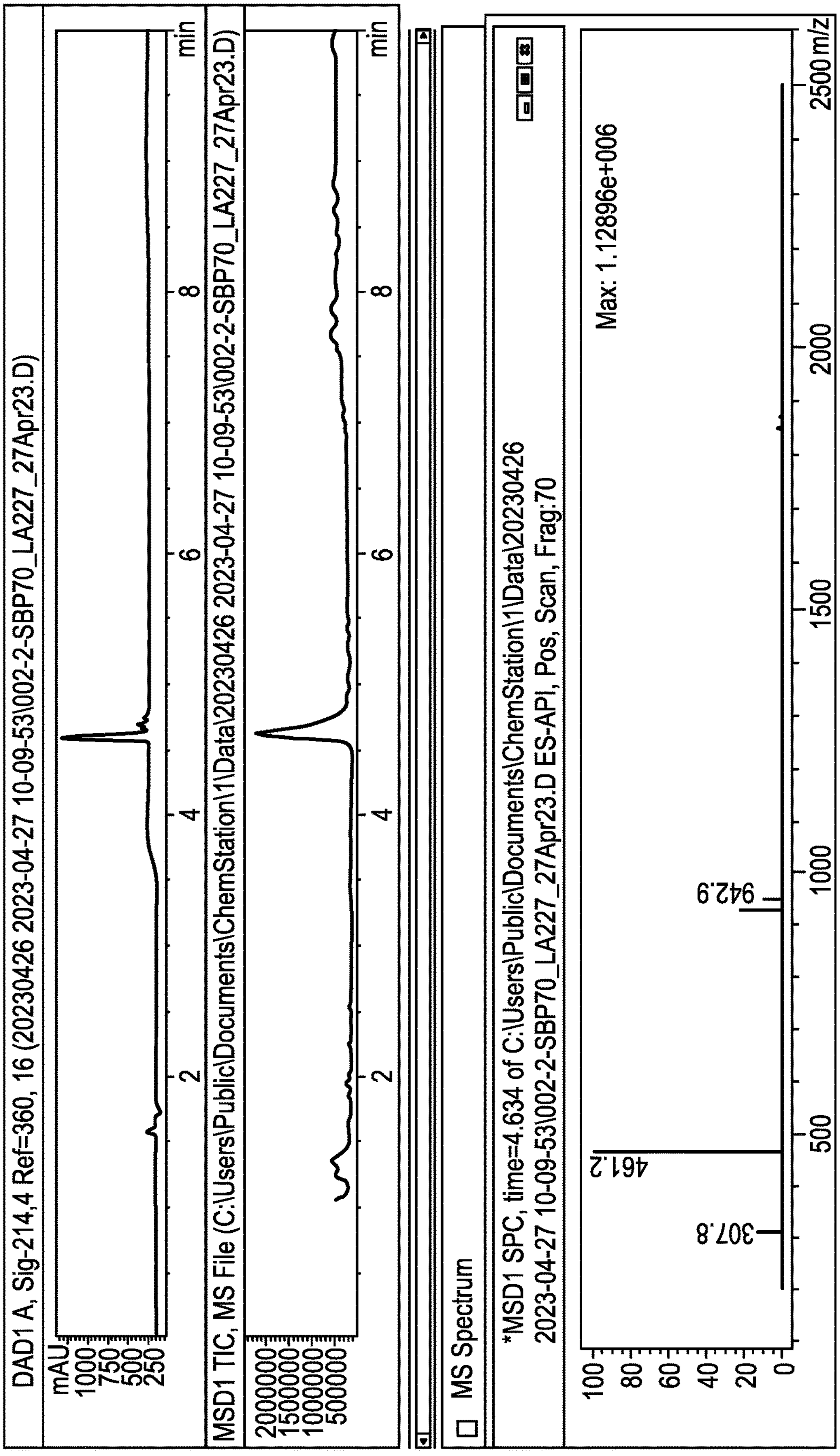
FIG. 4 shows LC-MS traces of SB-P-70.

A specific synthesis route for SB-P-70 is shown in FIG. 2. The 0.1 mmol scale synthesis of SB-P-70 was performed using double coupling methods for 1Lys, 2Val, 3Lys and 4Phe. Purification was performed at room temperature, using a gradient of 20 to 80% B over 30 minutes, monitored at 214 nm. Purity=91%, Yield=42%.

Unless otherwise stated herein, peptides were synthesised according to the general procedures above, in line with the exemplary procedures below, or were ordered directly.

Mortality Assessment Methods

Leaf Dip Assay Testing Against *Plutella xylostella*

The assay was carried out based on IRAC susceptibility test method 019 (irac online.org/methods/aphids-adultnymphs/).

Figure 5:
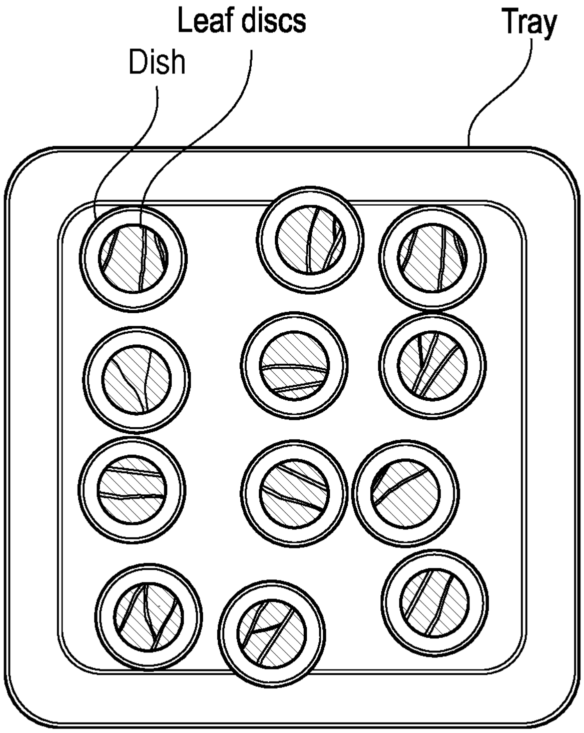
FIG. 5 shows the leaf dip assay experimental set up.
Figure 6:
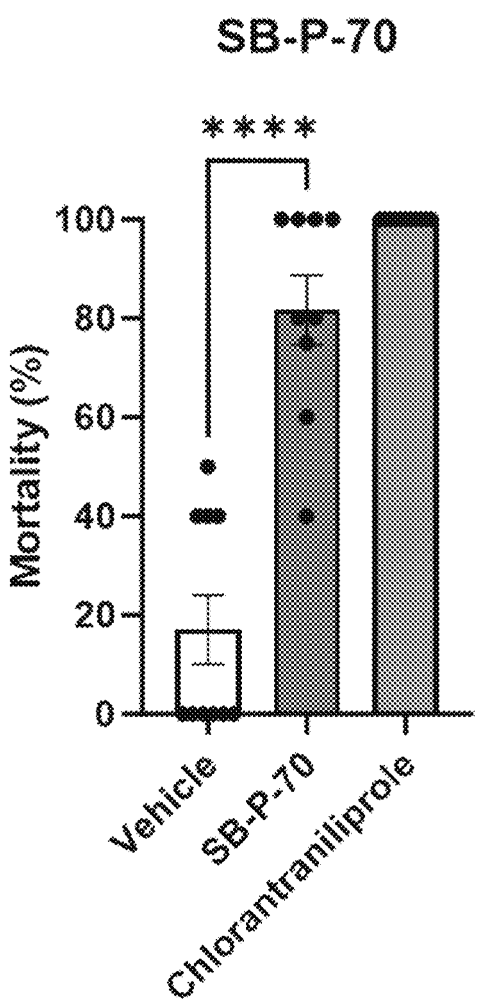
FIG. 6 shows activity data of unformulated SB-P-70 against *Plutella xylostella* after 96 hours.

Fill a small 4 cm wide 3 cm high dish with a 1% agar treatment solution of the active chemical or control (ensuring 1 cm gap between the agar and the lid) and leave to set. Dip a 2.5 cm leaf disc into 3 ml of treatment solution allowing the treatment to coat the leaf. Leave the disc to dry for 1 hour and place onto the set agar. Place insects (*Plutella xylostella*) onto each of the leaf discs. Each unit is sealed with a close-fitting, ventilated lid. Place the agar dishes in a small plastic tray lined with moist tissue paper and ensure the water trays in the bottom of the incubator are filled with clean water and place within the incubator. An assessment of mortality is made at 72, 96 and 120 hours. The leaf dip assay set up is shown in FIG. 5. Leaf dip assays were performed with SB-P-70, and compared to a negative control vehicle and a current commercial insecticide Chlorantraniliprole. The activity of SB-P-70 is shown in FIG. 6; SB-P-70 has good activity whilst being eco-friendly and targeted to specific pests unlike broad spectrum chemical insecticides such as Chlorantraniliprole.

Lepidoptera Artificial Diet Assay Against *Spodoptera frugiperda*

Figure 7:
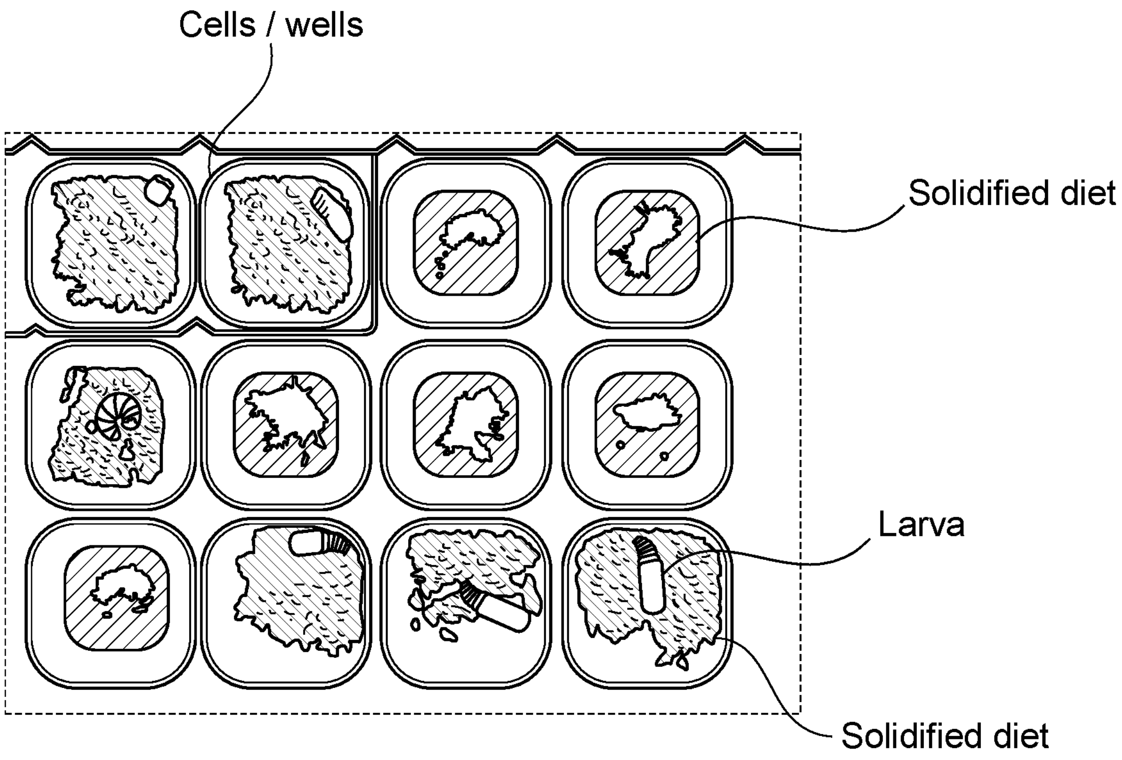
FIG. 7 shows the lepidoptera artificial diet assay experimental set up.
Figure 8:
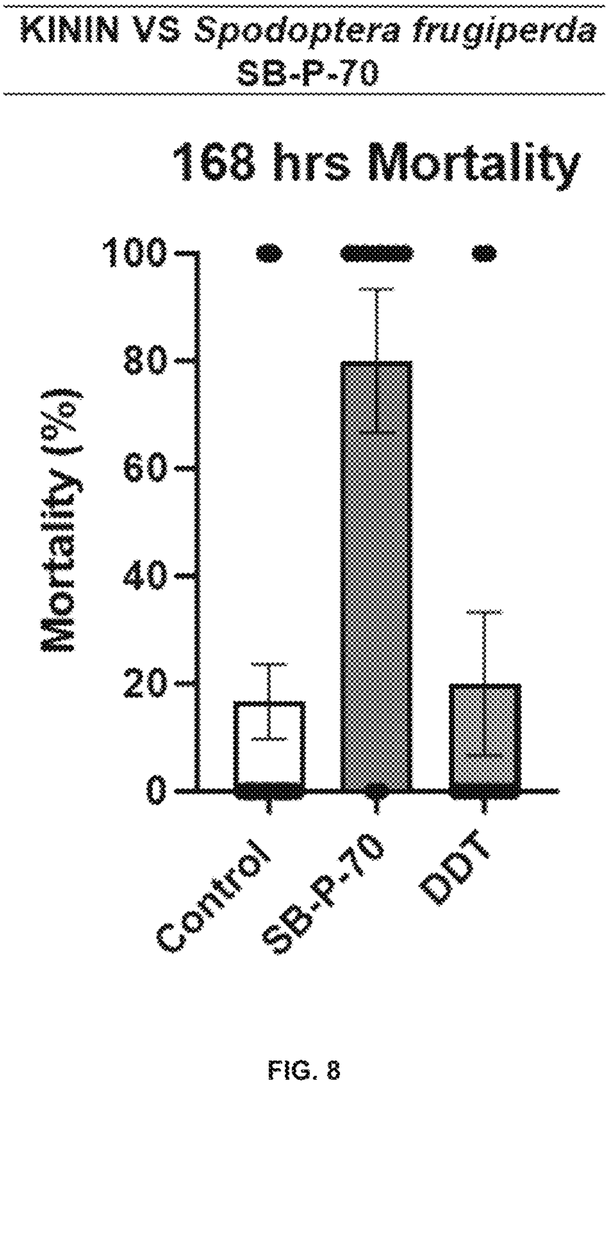
FIG. 8 shows activity data of unformulated SB-P-70 against *Spodoptera frugiperda* after 168 hours.

Frontier Lepidoptera artificial diet was made up by preparing agar at 1% and then mixing it with artificial diet powder. Peptide solution was aliquoted in 10 cells and diet poured straight onto it. The final concentration of the peptide was $1\times10^{-4}$ M, and each peptide was aliquoted in 10 cells. Once the diet solidified and cooled down, one L1 larvae was infested in each cell. The trays were sealed with heat and let larva were allowed to develop for 168 hrs. Finally, pupation and mortality were scored for. The lepidoptera artificial diet assay set up is shown in FIG. 7. Lepidoptera artificial diet assays were performed with SB-P-70, and compared to a negative control vehicle and the insecticide dichlorodiphenyltrichloroethane (DDT). The activity of SB-P-70 is shown in FIG. 8; SB-P-70 has much higher activity whilst being eco-friendly and targeted to specific pests unlike broad spectrum chemical insecticides such as DDT.

REFERENCES

A number of publications are cited in order to more fully describe and disclose the invention and the state of the art to which the invention pertains. Full citations for these references are provided below. The entirety of each of these references is incorporated herein by reference.

Koyama T, Terhzaz S, Naseem M T, Nagy S, Rewitz K, Dow J A T, Davies S A, Halberg K V. A nutrient-responsive hormonal circuit mediates an inter-tissue program regulating metabolic homeostasis in adult Drosophila. Nat Commun. 2021

Kean L, Cazenave W, Costes L, Broderick K E, Graham S, Pollock V P, Davies S A, Veenstra J A, Dow J A. Two nitridergic peptides are encoded by the gene capability in Drosophila melanogaster. Am J Physiol Regul Integr Comp Physiol. 2002

Yeoh J G C, Pandit A A, Zandawala M, Nässel D R, Davies S A, Dow JAT. DINeR: Database for Insect Neuropeptide Research. Insect Biochem Mol Biol. 2017

Ahn S J, Corcoran J A, Vander Meer R K, Choi M Y. Identification and Characterization of GPCRs for Pyrokinin and CAPA Peptides in the Brown Marmorated Stink Bug, *Halyomorpha halys* (Hemiptera: Pentatomidae). Front Physiol. 2020

Audsley N and Down R E, G protein coupled receptors as targets for next generation pesticides. Insect Biochem Molec 67: 27-37 (2015).

Halberg K A, Terhzaz S, Cabrero P, Davies S A and Dow JAT, Tracing the evolutionary origins of insect renal function. Nat Commun 6 (2015).

Dow J A, Insights into the Malpighian tubule from functional genomics. J Exp Biol 212: 435-445 (2009).

Huesmann G R, Cheung C C, Loi P K, Lee T D, Swiderek K M and Tublitz N J, Amino acid sequence of CAP2b, an insect cardioacceleratory peptide from the tobacco hawkmoth Manduca sexta. FEBS Lett 371: 311-314 (1995).

Davies S A, Cabrero P, Povsic M, Johnston N R, Terhzaz S and Dow JAT, Signaling by drosophila capa neuropeptides. Gen Comp Endocr 188: 60-66 (2013).

Terhzaz S, Teets N M, Cabrero P, Henderson L, Ritchie M G, Nachman R J, Dow JAT, Denlinger D L and Davies S A, Insect capa neuropeptides impact desiccation and cold tolerance. Proc Natl Acad Sci 201501518 (2015).

Terhzaz S, Alford L, Yeoh JGC, Marley R, Dornan A T, Dow JAT and Davies S A, Renal neuroendocrine control of desiccation and cold tolerance by *Drosophila suzukii*. Pest Manag Sci 74: 800-810 (2017).

Predel R, Wegener C, Biology of the CAPA peptides in insects. Cell Mol Life Sci 63: 2477-2490 (2006).

Lamango N S, Nachman R J, Hayes T K, Strey A and Isaac R E, Hydrolysis of insect neuropeptides by an angiotensin converting enzyme from the housefly, *M. domestica*. Peptides 18: 47-52 (1997).

Terhzaz S, Cabrero P, Robben J H, Radford J C, Hudson B D, Milligan G, Dow J A and Davies S A, Mechanism and function of Drosophila capa GPCR: a desiccation stress-responsive receptor with functional homology to human neuromedinU receptor. PLoS One 7(1): e29897 (2012).

Blackman R L and Eastop V F, Aphids on the World's Crops: An Identification Guide, John Wiley & Sons Ltd, Chichester, U K. (2000).

Dow JAT, Maddrell SHP, Gortz A, Skaer N J V, Brogan S and Kaiser K, The Malpighian tubules of Drosophila melanogaster—a novel phenotype for studies of fluid secretion and its control. J Exp Biol 197: 421-428 (1994).

Davies S A, Huesmann G R, Maddrell S H, O'Donnell M J, Skaer N J, Dow JAT and Tublitz N J, CAP2b, a cardioacceleratory peptide, is present in Drosophila and stimulates tubule fluid secretion via cGMP. Am J Physiol 269: R1321-R1326 (1995).

Beyenbach K W, Skaer H and Dow J A, The developmental, molecular, and transport biology of Malpighian tubules. Annu Rev Entomol 55: 351-374 (2010).

Sadeghi A., Van Damme, E. J. M. and Smagghe G. (2009) Evaluation of the susceptibility of the pea aphid, *Acyrthosiphon pisum*, to a selection of novel biorational insecticides using an artificial diet. Journal of Insect Science 9:65.

Van Emden F (2009). Artificial diet for aphids—thirty years' experience. REDIA, XCII: 163-167

SEQUENCE LISTING

```
Sequence total quantity: 16
SEQ ID NO: 1            moltype = AA  length = 8
FEATURE                 Location/Qualifiers
source                  1..8
                        mol_type = protein
                        note = Z peptide
                        organism = synthetic construct
SEQUENCE: 1
KVKFSAWG                                                            8

SEQ ID NO: 2            moltype = AA  length = 8
FEATURE                 Location/Qualifiers
source                  1..8
                        mol_type = protein
                        note = SB-P-70
                        organism = synthetic construct
MOD_RES                 8
                        note = glycinamide
SEQUENCE: 2
KVKFSAWG                                                            8

SEQ ID NO: 3            moltype = AA  length = 11
FEATURE                 Location/Qualifiers
source                  1..11
                        mol_type = protein
                        note = SB-P-47
                        organism = synthetic construct
MOD_RES                 11
                        note = leucinamide
MOD_RES                 1
                        note = pyroglutamyl-alanine
SEQUENCE: 3
AIMARPQVPR L                                                        11

SEQ ID NO: 4            moltype = AA  length = 8
FEATURE                 Location/Qualifiers
source                  1..8
                        mol_type = protein
                        note = SB-P-49
                        organism = synthetic construct
MOD_RES                 8
                        note = leucinamide
SEQUENCE: 4
SVPFKPRL                                                            8

SEQ ID NO: 5            moltype = AA  length = 19
FEATURE                 Location/Qualifiers
source                  1..19
                        mol_type = protein
                        note = SB-P-51
                        organism = synthetic construct
MOD_RES                 19
                        note = leucinamide
SEQUENCE: 5
LRQLQSNGEP AYRVRTPRL                                                19
```

-continued

```
SEQ ID NO: 6            moltype = AA  length = 16
FEATURE                 Location/Qualifiers
source                  1..16
                        mol_type = protein
                        note = SB-P-80
                        organism = synthetic construct
MOD_RES                 16
                        note = leucinamide
SEQUENCE: 6
NADEDQQQSV DFTPRL                                                     16

SEQ ID NO: 7            moltype = AA  length = 10
FEATURE                 Location/Qualifiers
source                  1..10
                        mol_type = protein
                        note = SB-P-81
                        organism = synthetic construct
MOD_RES                 10
                        note = leucinamide
SEQUENCE: 7
GGSMTFSPRL                                                            10

SEQ ID NO: 8            moltype = AA  length = 12
FEATURE                 Location/Qualifiers
source                  1..12
                        mol_type = protein
                        note = SB-P-46
                        organism = synthetic construct
MOD_RES                 12
                        note = leucinamide
SEQUENCE: 8
SPPYSPPFSP RL                                                         12

SEQ ID NO: 9            moltype = AA  length = 10
FEATURE                 Location/Qualifiers
source                  1..10
                        mol_type = protein
                        note = SB-P-65
                        organism = synthetic construct
MOD_RES                 10
                        note = glycinamide
SEQUENCE: 9
RQKTVFSSWG                                                            10

SEQ ID NO: 10           moltype = AA  length = 7
FEATURE                 Location/Qualifiers
source                  1..7
                        mol_type = protein
                        note = SB-P-66
                        organism = synthetic construct
MOD_RES                 7
                        note = glycinamide
SEQUENCE: 10
PAFSSWG                                                               7

SEQ ID NO: 11           moltype = AA  length = 9
FEATURE                 Location/Qualifiers
source                  1..9
                        mol_type = protein
                        note = SB-P-86
                        organism = synthetic construct
MOD_RES                 9
                        note = glycinamide
MOD_RES                 1
                        note = pyroglutamyl-leucine
SEQUENCE: 11
LTFTSSWGG                                                             9

SEQ ID NO: 12           moltype = AA  length = 8
FEATURE                 Location/Qualifiers
source                  1..8
                        mol_type = protein
                        note = SB-P-039
                        organism = synthetic construct
MOD_RES                 1
                        note = palmitoyl-glutamine
MOD_RES                 8
                        note = tryptophanamide
SEQUENCE: 12
```

-continued

```
QLTFSPDW                                                                  8

SEQ ID NO: 13             moltype = AA  length = 7
FEATURE                   Location/Qualifiers
source                    1..7
                          mol_type = protein
                          note = SB-P-042
                          organism = synthetic construct
MOD_RES                   1
                          note = pyroglutamyl-leucine
MOD_RES                   7
                          note = tryptophanamide
SEQUENCE: 13
LTFSPDW                                                                   7

SEQ ID NO: 14             moltype = AA  length = 6
FEATURE                   Location/Qualifiers
source                    1..6
                          mol_type = protein
                          note = SB-P-69
                          organism = synthetic construct
MOD_RES                   6
                          note = glycinamide
SEQUENCE: 14
NFSPWG                                                                    6

SEQ ID NO: 15             moltype = AA  length = 19
FEATURE                   Location/Qualifiers
source                    1..19
                          mol_type = protein
                          note = SB-P-48
                          organism = synthetic construct
MOD_RES                   19
                          note = leucinamide
SEQUENCE: 15
EQNVQSNGEP AYRVRTPRL                                                      19

SEQ ID NO: 16             moltype = AA  length = 8
FEATURE                   Location/Qualifiers
source                    1..8
                          mol_type = protein
                          note = SB-P-41
                          organism = synthetic construct
MOD_RES                   8
                          note = tryptophanamide
SEQUENCE: 16
QLTFSPDW                                                                  8
```

The invention claimed is:

1. A method of inhibiting infestation of a plant by *Plutella xylostella* insects, the method comprising contacting the plant or a part thereof, or a site on which the plant is growing or is intended to be grown, with a compound having the formula below, or a salt or solvate thereof:

[Hy]-KVKFSAWG-[NH2] (SEQ ID NO:2), wherein Hy is hydrogen, or a composition comprising an effective amount of the compound in admixture with one or more solvents, carriers, diluents, adjuvants, preservatives, dispersants, emulsifying agents, or synergists, wherein the compound or the composition contacts the *Plutella xylostella* insects, and wherein the method increases the mortality of the *Plutella xylostella* insects, thereby inhibiting *Plutella xylostella* insect infestation of the plant.

2. The method according to claim 1, wherein the compound or composition is contacted with the plant or part thereof, or a site on which the plant is growing or is intended to be grown, while the plant or part is free of insects.

3. The method according to claim 1, wherein contacting the plant or part thereof, or site, comprises watering, feeding, spraying, atomizing, foaming, fogging, culturing in hydroculture, culturing in hydroponics, coating, submerging, and/or encrusting the plant or part thereof, or site with the compound or composition.

4. The method according to claim 1, wherein the composition is an aqueous composition.

5. The method according to claim 3, wherein the plant or part thereof, or site, is contacted with a concentration of the compound of between $10^{-3}$ M to $10^{-9}$ M.

6. A method of reducing or treating an insect infestation of a plant, or of reducing insect load on a plant, wherein the insect is *Plutella xylostella*, the method comprising contacting the plant or a part thereof, or a site on which the plant is growing, with a compound having the formula below, or a salt or solvate thereof:

[Hy]-KVKFSAWG-[NH2] (SEQ ID NO:2), wherein Hy is hydrogen, or a composition comprising an effective amount of the compound in admixture with one or more solvents, carriers, diluents, adjuvants, preservatives, dispersants, emulsifying agents, or synergists, wherein the compound or the composition contacts the *Plutella xylostella* insects, and wherein the method increases the mortality of the *Plutella xylostella* insects, thereby reducing or treating *Plutella xylostella* insect infestation of the plant or reducing *Plutella xylostella* insect load on the plant.

7. The method according to claim 6, wherein contacting the plant or part thereof, or site, comprises watering, feeding, spraying, atomizing, foaming, fogging, culturing in hydroculture, culturing in hydroponics, coating, submerging, and/or encrusting the plant or part thereof, or site with the compound or composition.

8. The method according to claim 6, wherein the composition is an aqueous composition.

9. The method according to claim 7, wherein the plant or part thereof, or site, is contacted with a concentration of the compound of between $10^{-3}$ M to $10^{-9}$ M.

* * * * *